(12) United States Patent
Takemura et al.

(10) Patent No.: US 7,176,313 B2
(45) Date of Patent: Feb. 13, 2007

(54) ANTI ACID-FAST BACTERIAL AGENT CONTAINING PYRIDONECARBOXYLIC ACIDS AS ACTIVE INGREDIENT

(75) Inventors: Makoto Takemura, Edogawa-ku (JP); Hisashi Takahashi, Edogawa-ku (JP); Katsuhiro Kawakami, Edogawa-ku (JP); Kenji Namba, Edogawa-ku (JP); Mayumi Tanaka, Edogawa-ku (JP); Rie Miyauchi, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/203,199

(22) PCT Filed: Feb. 7, 2001

(86) PCT No.: PCT/JP01/00861

§ 371 (c)(1),
(2), (4) Date: Aug. 7, 2002

(87) PCT Pub. No.: WO01/53376

PCT Pub. Date: Aug. 16, 2001

(65) Prior Publication Data

US 2003/0119848 A1 Jun. 26, 2003

(30) Foreign Application Priority Data

Feb. 9, 2000 (JP) .............................. 2000-038099

(51) Int. Cl.
C07D 401/04 (2006.01)
(52) U.S. Cl. ................. 544/363; 514/253.08; 544/101; 544/231; 544/351; 544/362
(58) Field of Classification Search ................ 544/363, 544/230, 105; 514/253.08, 312, 300, 230.5; 546/156, 113
See application file for complete search history.

(56) References Cited

U.S. PATENT DOCUMENTS

| 4,777,253 A | | 10/1988 | Mitscher et al. |
| 5,519,016 A | * | 5/1996 | Kimura et al. ......... 514/210.21 |
| 5,607,942 A | | 3/1997 | Petersen et al. |

FOREIGN PATENT DOCUMENTS

| EP | 0 195 841 A1 | 10/1986 |
| EP | 0 226 961 A1 | 7/1987 |
| EP | 0 230 295 A2 | 7/1987 |
| EP | 0 191 185 A1 | 8/1988 |
| EP | 0341439 | 4/1989 |
| EP | 0 319 906 A2 | 6/1989 |
| EP | 0 341 493 A2 | 11/1989 |
| EP | 0 352 123 A2 | 1/1990 |
| EP | 0 357 047 A1 | 3/1990 |
| EP | 0 603 887 A2 | 6/1994 |
| EP | 0 641 793 A1 | 3/1995 |
| EP | 1 258 478 A1 | 11/2002 |
| EP | 1 298 131 A1 | 4/2003 |
| GB | 2 188 317 A | 9/1987 |
| JP | 3-24013 | * | 2/1991 |
| JP | 3-81224 | | 4/1991 |
| JP | 6-239857 A | | 8/1994 |
| JP | 6-271568 | * | 9/1994 |
| JP | 8-333337 A | | 12/1996 |
| WO | WO 96/38147 | | 12/1996 |

OTHER PUBLICATIONS

Klopman et al. Chem. Abs. 125:322777 (1996).*
Alangaden et al. Chem. Abs. 123:138587 (1995).*
Nakano et al. Chemical Abstracts, vol. 115, No. 142273 (1991) Abstract for JP 03024013.*
Ito et al. Chemical Abstracts, vol. 122, No. 374736 (1995) Abstract for JP 06271568.*
Hagihara et al. Bioorganic & Medicinal Chemistry Letters, vol. 9, p. 3063-3068 (1999).*
Berline, O. George W. et al. "In vitro activity of six fluorinated quinolones against *Mycobacterium tuberculosis* ", J. Antimicrob. Chemother. 1997), vol. 19, No. 5, pp. 611 to 615.
Patty, S.R. et al., "In vitro activity of five new quinolones against cultivable mycobacteria" Eur. J. Clin. Microbiol. (1987), vol. 6, No. 5, pp. 572 to 573.
Franblau, Scott G. et al., "Comparative in vitro activities of 20 fluoroquinolones against *Mycobacterium leprae*", Antimicrob. Agents Chemother. (1990), vol. 34, No. 2, pp. 229 to 231.
Rerau, Thomas E. et al., "Structure-activity relationships of quinolone agents against mycobacteria: effect of structural modifications at the 8 position", Antimicrob. Agents Chemother. (1996), vol. 40, No. 10, pp. 2363 to 2368.

(Continued)

Primary Examiner—Emily Bernhardt
(74) Attorney, Agent, or Firm—Sughrue Mion, PLLC

(57) ABSTRACT

An anti acid-fast bacterial agent containing, as an active ingredient, a pyridonecarboxylic acid derivative represented by the following general formula (1), a salt thereof, or a hydrate thereof, which shows excellent antibacterial activity against *Mycobacterium tuberculosis* and atypical acid-fast bacteria and exhibits good pharmacokinetics and safety

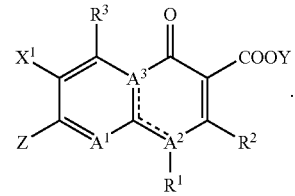

(1)

1 Claim, No Drawings

OTHER PUBLICATIONS

Tomioka, Haruaki et al., "Comparative in vitro antimicrobial activities of the newly synthesized quinolone HSR-903, sitafloxacin (DU-6859a), gatifloxacin (AM-1155), and levofloxacin against *Mycobacterium tuberculosis* and *Mycobacterium avium* complex", Antimicrob, Agents Chemother. (1999), vol. 43, No. 12, pp. 3001 to 3004.
XP-002227254 (1990) Abstract.
XP-002227255 (1999) Abstract.
XP-002227256 (1990) Abstract.
XP-002227257 (1993) Abstract.
XP-002227258 (1995) Abstract.
XP-002227259 (1990) Abstract.
XP-002238724, Xilin Zhao et al., "Killing of *Staphylococcus aureus* by c-8-Methoxy Fluoroquinolones", Antimicrobial Agents and Chemotherapyl, vol. 42, No. 4, 1998, pp. 956-958.
XP-000654032, Isao Hayakawa et al., "Synthesis and Antibacterial Activities of Substituted 7-Oxo-2,3-dihydro-7H-pyrido[1,2,3-de][1,4]benzoxazine-6-carboxylic Acids", Chemical and Pharmaceutical Bulletin, Pharmaceutical Society of Japan, vol. 32, No. 12, 1984, pp. 4907-4913.
Patent Abstracts of Japan—06049059 (1994).
Patent Abstracts of Japan—06271568 (1994).
Patent Abstracts of Japan—58072589 (1983).
Supplementary Partial European Search Report dated May 15, 2003.
XP-002227260 (1995) Abstract.
XP-002227261 (1991) Abstract.
XP-002227262 (1996) Abstract.
Partial European Search Report dated Feb. 3, 2003.

* cited by examiner

ANTI ACID-FAST BACTERIAL AGENT CONTAINING PYRIDONECARBOXYLIC ACIDS AS ACTIVE INGREDIENT

TECHNICAL FIELD

The present invention relates to an anti acid-fast bacterial agent containing, as the active ingredient, a pyridonecarboxylic acid derivative, a pharmaceutically acceptable salt thereof, or a hydrate thereof, which shows excellent antibacterial activity against *Mycobacterium tuberculosis* and a typical acid-fast bacteria.

BACKGROUND OF THE INVENTION

Even in recent years, a *Mycobacterium tuberculosis*-infected disease (hereinafter referred to as tuberculosis) is one of extremely serious diseases in the world. The progress of the treatment of tuberculosis was started with the discovery of streptomycin (SM), and then antituberculous action of p-aminosalicylic acid (PAS), isoniazid (INH) and rifampicin (RFP) was found. By combined use thereof, most of tuberculosis became treatable and therefore, advanced countries succeeded in rapid decrease of tuberculosis from 1950s. However, lately, with the prevalence of HIV infection, tuberculosis has rapidly increased in Africa and Southeast Asia, and the spread of multidrug resistant tuberculosis has been reported in Japan and USA. In addition, patients of infectious diseases caused by a typical acid-fast bacteria, especially *Mycobacterium avium*-intracellulare complex (*M. avium*-intracellulare complex: MAC) tend to increase year by year.

Chemotherapeutic agents currently used for tuberculosis or a typical acid-fast bacterial diseases include RFP, INH, SM, PAS, ethambutol (EB), kanamycin (KM), ethionamide (ETH), pyrazinamide (PZA), enviomycin (EVM), capreomycin (CPRM), cycloserine (CS), prothionamide (PTH), viomycin (VM), and the like, and these pharmaceutical agents are generally used at polypharmacy.

However, they exhibit unsatisfactory effectiveness and safety, for example, insufficient antibacterial activity against multidrug resistant *Mycobacterium tuberculosis* and toxicity toward lever, kidney, etc.

Under such circumstances, there is anxiety that pathology of these infectious diseases becomes complex and intractable, and therefore, it is strongly desired to promptly develop an effective therapeutic agent which is excellent in antibacterial activity and exhibits no cross resistance.

An object of the invention is to provide a pyridonecarboxylic acid which shows excellent antibacterial activity against *Mycobacterium tuberculosis* and a typical acid-fast bacteria and exhibits good pharmacokinetics and safety.

Prior patent applications, which is directed to pyridonecarboxylic acid-type synthetic antibacterial agents, all describe pharmaceutical agents against so-called general bacteria such as Gram-negative and Gram-positive bacteria but they describe no action against acid-fast bacteria.

DISCLOSURE OF THE INVENTION

The present inventors have extensively examined in order to provide compounds which have high antibacterial activity against acid-fast bacteria such as *Mycobacterium tuberculosis* and a typical acid-fast bacteria and is also excellent in safety. As a result, they have found that a pyridonecarboxylic acid represented by the following general formula (1) has good antibacterial activity against acid-fast bacteria, and thus accomplished the invention.

Namely, the invention relates to an anti acid-fast bacterial agent containing a compound represented by the following general formula (1), a salt thereof, or a hydrate thereof as an active ingredient.

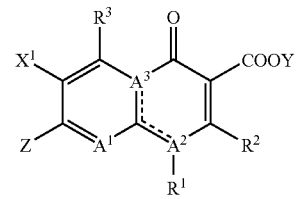

[wherein, $R^1$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have substituent(s), an aryl group having 6 to 10 carbon atoms which may have substituent(s), a heteroaryl group which may have substituent(s) (the group being a 5- or 6-membered ring and containing 1 to 4 heteroatoms optionally selected from nitrogen atom, oxygen atom, and sulfur atom), an alkoxy group having 1 to 6 carbon atoms, or an alkylamino group having 1 to 6 carbon atoms, $R^2$ represents hydrogen atom or an alkylthio group having 1 to 6 carbon atoms, the $R^1$ and $R^2$ may be combined so as to form a cyclic structure with including a part of the mother nucleus, and the ring may contain a sulfur atom as a ring-constituting atom, and further, the ring may have an alkyl group having 1 to 6 carbon atoms as a substituent.

$R^3$ represents hydrogen atom, amino group, thiol group, a halogenomethyl group, an alkyl group having 1 to 6 carbon atoms, an alkenyl group having 2 to 6 carbon atoms, an alkynyl group having 2 to 6 carbon atoms, or an alkoxy group having 1 to 6 carbon atoms, among them, the amino group may have one or more groups selected from formyl group, an alkyl group having 1 to 6 carbon atoms, and an acyl group having 2 to 5 carbon atoms as substituent(s).

$A^1$ represents nitrogen atom or a partial structure represented by the formula (2)

(wherein, $X^2$ represents hydrogen atom, amino group, a halogen atom, cyano group, a halogenomethyl group, a halogenomethoxy group, an alkyl group having 1 to 6 carbon atoms, an alkenyl group having 2 to 6 carbon atoms, an alkynyl group having 2 to 6 carbon atoms, or an alkoxy group having 1 to 6 carbon atoms, among them, the amino group may have one or more groups selected from formyl group, an alkyl group having 1 to 6 carbon atoms, and an acyl group having 2 to 5 carbon atoms as substituent(s);

further, the $X^2$ and the above $R^1$ may be combined so as to form a cyclic structure with including a part of the mother nucleus, and the ring thus formed may contain oxygen atom, nitrogen atom, or sulfur atom as a ring-constituting atom, and moreover, the ring may have an alkyl group having 1 to 6 carbon atoms or a halogenoalkyl group having 1 to 6 carbon atoms as a substituent).

$A^2$ and $A^3$ each represents nitrogen atom or carbon atom, and $A^1$, $A^2$ and $A^3$ form a partial structure

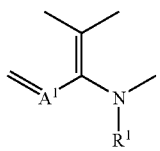

or a partial structure

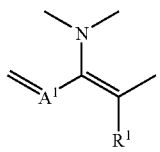

together with the carbon atoms which are combined therewith.

$X^1$ represents a halogen atom, hydrogen atom, or amino group,

Y represents hydrogen atom, phenyl group, acetoxymethyl group, pivaloyloxymethyl group, ethoxycarbonyl group, choline group, dimethylaminoethyl group, 5-indanyl group, phthalidinyl group, a 5-alkyl-2-oxo-1,3-dioxol-4-ylmethyl group, 3-acetoxy-2-oxobutyl group, an alkyl group having 1 to 6 carbon atoms, an alkoxymethyl group having 2 to 7 carbon atoms, or a phenylalkyl group which is constituted by an alkylene group having 1 to 6 carbon atoms and phenyl group, Z represents a monocyclic, bicyclic, or tricyclic heterocyclic substituent, and the heterocyclic substituent is saturated, partially saturated or unsaturated one, may contain one or more heteroatoms selected from the group consisting of nitrogen atom, oxygen atom, and sulfur atom, and further, may form a bicyclo structure or a spiro structure.

Further, the heterocyclic substituent may be substituted by one or more groups selected from the group consisting of a halogen atom, amino group, hydroxyl group, carbamoyl group, an alkyl group having 1 to 6 carbon atoms, an alkylamino group having 1 to 6 carbon atoms, an aryl group having 6 to 10 carbon atoms, a heteroaryl group (which is a 5- or 6-membered ring and contains 1 to 4 heteroatoms optionally selected from nitrogen atom, oxygen atom, and sulfur atom), an alkoxy group having 1 to 6 carbon atoms, an alkylthio group having 1 to 6 carbon atoms, a halogenoalkyl group having 1 to 6 carbon atoms, and an aminoalkyl group having 1 to 6 carbon atoms, and the alkyl group or the alkyl moiety of the alkylamino group, alkoxy group, alkylthio group, halogenoalkyl group, and aminoalkyl group may have a cyclic structure, further, may have one or more groups selected from the group consisting of a halogen atom, an alkyl group having 1 to 6 carbon atoms, an alkoxy group having 1 to 6 carbon atoms, an aryl group having 6 to 10 carbon atoms, and a heteroaryl group (which is a 5- or 6-membered ring and contains 1 to 4 heteroatoms optionally selected from nitrogen atom, oxygen atom, and sulfur atom) as substituent(s).

The amino moiety of the amino group, aminoalkyl group, and alkylamino group may have one or two alkyl groups having 1 to 6 carbon atoms (the alkyl group may have a cyclic structure, and may have one or more groups selected from the group consisting of hydroxyl group, a halogen atom, an alkylthio group having 1 to 6 carbon atoms, and an alkoxy group having 1 to 6 carbon atoms as substituent(s))(when two alkyl groups are present, they may be the same or different), and the amino moiety may be protected by a protective group.

All the above aryl groups and heteroaryl groups may have one or more groups selected from the group consisting of a halogen atom, hydroxyl group, thiol group, amino group, nitro group, cyano group, carboxyl group, carbamoyl group, phenyl group, an alkyl group having 1 to 6 carbon atoms, an alkoxy group having 1 to 6 carbon atoms, an alkylthio group having 1 to 6 carbon atoms, an alkoxycarbonyl group having 2 to 6 carbon atoms, an acyl group having 2 to 5 carbon atoms, and a heteroaryl group (which is a 5- or 6-membered ring and contains 1 to 4 heteroatoms optionally selected from nitrogen atom, oxygen atom, and sulfur atom) as substituent(s), these alkyl group, alkoxy group, alkylthio group, alkoxycarbonyl group, acyl group, phenyl group, and heteroaryl group (which is a 5- or 6-membered ring and contains 1 to 4 heteroatoms optionally selected from nitrogen atom, oxygen atom, and sulfur atom) may have one or more groups selected from the group consisting of a halogen atom, hydroxyl group, an alkoxy group having 1 to 6 carbon atoms, and an alkylthio group having 1 to 6 carbon atoms as substituent(s), and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).]

Furthermore, the invention relates to the following.

The anti acid-fast bacterial agent wherein the compound represented by the formula (1) is a compound represented by the following formula

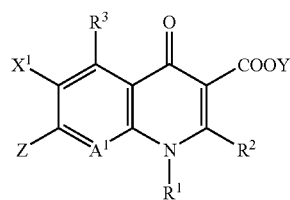

or the following formula

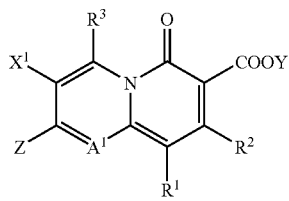

(wherein A¹, R¹, R², R³, X¹, Y, and Z are the same as the above definitions);

The anti acid-fast bacterial agent wherein the compound represented by the formula (1) is a compound represented by the following formula

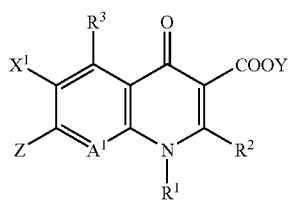

(wherein, A¹ R¹, R², R³, X¹, Y, and Z are the same as the above definitions);

The anti acid-fast bacterial agent wherein Y is hydrogen atom;

The anti acid-fast bacterial agent wherein R¹ is an alkyl group having 1 to 6 carbon atoms, a halogenoalkyl group having 1 to 6 carbon atoms, a cyclic alkyl group having 3 to 6 carbon atoms which may have substituent(s), or an aryl group having 6 to 10 carbon atoms which may have substituent(s);

The anti acid-fast bacterial agent wherein R¹ and R² may be combined so as to form a cyclic structure with including a part of the mother nucleus (the ring may contain a sulfur atom as a ring-constituting atom, and further may have an alkyl group having 1 to 6 carbon atoms as a substituent);

The anti acid-fast bacterial agent wherein R³ is hydrogen atom, amino group, or an alkyl group having 1 to 6 carbon atoms;

The anti acid-fast bacterial agent wherein A¹ is nitrogen atom or a partial structure represented by the formula (2);

 (2)

(wherein, X² represents hydrogen atom, a halogen atom, a halogenomethoxy group, an alkyl group having 1 to 6 carbon atoms, or an alkoxy group having 1 to 6 carbon atoms, the X² and the above R¹ may be combined so as to form a cyclic structure with including a part of the mother nucleus, and the ring thus formed may contain an oxygen atom as a ring-constituting atom, and further, the ring may have an alkyl group having 1 to 6 carbon atoms as a substituent)

The anti acid-fast bacterial agent wherein X¹ is a halogen atom or hydrogen;

The anti acid-fast bacterial agent wherein the compound represented by the formula (1) is a 6-carboxy-9-fluoro-2,3-dihydro-3-(S)-methyl-7-oxo-7H-pyrido[1,2,3-de][1.4]benzoxazine derivative having Z at the 10-position;

The anti acid-fast bacterial agent wherein the compound represented by the formula (1) is an 8-amino-6-carboxy-9-fluoro-2,3-dihydro-3-(S)-methyl-7-oxo-7H-pyrido[1,2,3-de][1.4]benzoxazine derivative having Z at the 10-position;

The anti acid-fast bacterial agent wherein the compound represented by the formula (1) is a 3-carboxy-6-fluoro-1-[2-(S)-fluoro-1-(R)-cyclopropyl]-1,4-dihydro-4-oxo-1,8-naphthyridine derivative having Z at the 7-position;

The anti acid-fast bacterial agent wherein the compound represented by the formula (1) is a 3-carboxy-8-chloro-6-fluoro-1-[2-(S)-fluoro-1-(R)-cyclopropyl]-1,4-dihydro-4-oxoquinoline derivative having Z at the 7-position The anti acid-fast bacterial agent wherein the compound represented by the formula (1) is a 3-carboxy-6-fluoro-1-[2-(S)-fluoro-1-(R)-cyclopropyl]-8-methoxy-1,4-dihydro-4-oxoquinoline derivative having Z at the 7-position;

The anti acid-fast bacterial agent wherein the compound represented by the formula (1) is a 3-carboxy-1-[2-(S)-fluoro-1-(R)-cyclopropyl]-8-methoxy-1,4-dihydro-4-oxoquinoline derivative having Z at the 7-position;

The anti acid-fast bacterial agent wherein the compound represented by the formula (1) is a 3-carboxy-6-fluoro-1-[2-(S)-fluoro-1-(R)-cyclopropyl]-8-difluoromethoxy-1,4-dihydro-4-oxoquinoline derivative having Z at the 7-position;

The anti acid-fast bacterial agent wherein the compound represented by the formula (1) is a 3-carboxy-1-[2-(S)-fluoro-1-(R)-cyclopropyl]-8-difluoromethoxy-1,4-dihydro-4-oxoquinoline derivative having Z at the 7-position;

The anti acid-fast bacterial agent wherein the compound represented by the formula (1) is a 3-carboxy-6-fluoro-1-[2-(S)-fluoro-1-(R)-cyclopropyl]-8-methyl-1,4-dihydro-4-oxoquinoline derivative having Z at the 7-position;

The anti acid-fast bacterial agent wherein the compound represented by the formula (1) is a 5-amino-3-carboxy-6-fluoro-1-[2-(S)-fluoro-1-(R)-cyclopropyl]-8-methoxy-1,4-dihydro-4-oxoquinoline derivative having Z at the 7-position;

The anti acid-fast bacterial agent wherein the compound represented by the formula (1) is a 5-amino-3-carboxy-6-fluoro-1-[2-(S)-fluoro-1-(R)-cyclopropyl]-8-methyl-1,4-dihydro-4-oxoquinoline derivative having Z at the 7-position;

The anti acid-fast bacterial agent wherein the compound represented by the formula (1) is a 5-amino-3-carboxy-6,8-difluoro-1-[2-(S)-fluoro-1-(R)-cyclopropyl]-1,4-dihydro-4-oxoquinoline derivative having Z at the 7-position;

The anti acid-fast bacterial agent wherein the compound represented by the formula (1) is a 3-carboxy-8-chloro-6-fluoro-1-cyclopropyl-1,4-dihydro-4-oxoquinoline derivative having Z at the 7-position;

The anti acid-fast bacterial agent wherein the compound represented by the formula (1) is a 3-carboxy-6-fluoro-1-cyclopropyl-8-methoxy-1,4-dihydro-4-oxoquinoline derivative having Z at the 7-position;

The anti acid-fast bacterial agent wherein the compound represented by the formula (1) is a 3-carboxy-1-cyclopropyl-8-methoxy-1,4-dihydro-4-oxoquinoline derivative having Z at the 7-position;

The anti acid-fast bacterial agent wherein the compound represented by the formula (1) is a 3-carboxy-6-fluoro-1- cyclopropyl-8-difluoromethoxy-1,4-dihydro-4-oxoquinoline derivative having Z at the 7-position;

The anti acid-fast bacterial agent wherein the compound represented by the formula (1) is a 3-carboxy-1-cyclopropyl-8-difluoromethoxy-1,4-dihydro-4-oxoquinoline derivative having Z at the 7-position;

The anti acid-fast bacterial agent wherein the compound represented by the formula (1) is a 3-carboxy-6-fluoro-1-cyclopropyl-8-methyl-1,4-dihydro-4-oxoquinoline derivative having Z at the 7-position;

The anti acid-fast bacterial agent wherein the compound represented by the formula (1) is a 5-amino-3-carboxy-6-fluoro-1-cyclopropyl-8-methoxy-1,4-dihydro-4-oxoquinoline derivative having Z at the 7-position;

The anti acid-fast bacterial agent wherein the compound represented by the formula (1) is a 5-amino-3-carboxy-6-fluoro-1-cyclopropyl-8-methyl-1,4-dihydro-4-oxoquinoline derivative having Z at the 7-position;

The anti acid-fast bacterial agent wherein the compound represented by the formula (1) is a 5-amino-3-carboxy-6,8-difluoro-1-cyclopropyl-1,4-dihydro-4-oxoquinoline derivative having Z at the 7-position;

The anti acid-fast bacterial agent wherein Z is a heterocyclic substituent represented by the following formula (3);

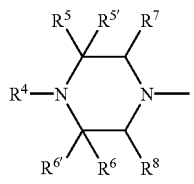

(wherein, $R^4$, $R^5$, and $R^6$ each independently represents hydrogen atom or an alkyl group having 1 to 6 carbon atoms,
the alkyl group may have one or more groups selected from the group consisting of hydroxyl group, a halogen atom, amino group, carbamoyl group, an alkylthio group having 1 to 6 carbon atoms, an alkoxy group having 1 to 6 carbon atoms, an alkylamino group having 1 to 6 carbon atoms, a halogenoalkyl group having 1 to 6 carbon atoms, and an aminoalkyl group having 1 to 6 carbon atoms as substituent(s),
the alkyl group or the alkyl moiety of the alkylamino group, alkoxy group, alkylthio group, halogenoalkyl group, and aminoalkyl group may have a cyclic structure,
further, may have one or more groups selected from the group consisting of a halogen atom, an alkyl group having 1 to 6 carbon atoms, and an alkoxy group having 1 to 6 carbon atoms as substituent(s).

The amino moiety of the amino group, aminoalkyl group, and alkylamino group may have one or two alkyl groups having 1 to 6 carbon atoms (the alkyl group may have a cyclic structure, and may have one or more groups selected from the group consisting of hydroxyl group, a halogen atom, an alkylthio group having 1 to 6 carbon atoms, and an alkoxy group having 1 to 6 carbon atoms as substituent(s)) (when two alkyl groups are present, they may be the same or different), and the amino moiety may be protected by a protective group.

$R^{5'}$ and $R^{6'}$ each independently represents hydrogen atom, an aryl group having 6 to 10 carbon atoms, or a heteroaryl group (which is a 5- or 6-membered ring and contains 1 to 4 heteroatoms optionally selected from nitrogen atom, oxygen atom, and sulfur atom) as substituent(s), the aryl group and heteroaryl group may have one or more groups selected from the group consisting of a halogen atom, hydroxyl group, thiol group, amino group, nitro group, cyano group, carboxyl group, carbamoyl group, phenyl group, an alkyl group having 1 to 6 carbon atoms, an alkoxy group having 1 to 6 carbon atoms, an alkylthio group having 1 to 6 carbon atoms, an alkoxycarbonyl group having 2 to 6 carbon atoms, an acyl group having 2 to 5 carbon atoms, and a heteroaryl group (which is a 5- or 6-membered ring and contains 1 to 4 heteroatoms optionally selected from nitrogen atom, oxygen atom, and sulfur atom) as substituent(s), among them, the alkyl group, alkoxy group, alkylthio group, alkoxycarbonyl group, acyl group, phenyl group, and heteroaryl group may have one or more groups selected from the group consisting of a halogen atom, hydroxyl group, an alkoxy group having 1 to 6 carbon atoms, and an alkylthio group having 1 to 6 carbon atoms as substituent(s), and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).

$R^7$ and $R^8$ each independently represents hydrogen atom or an alkyl group having 1 to 6 carbon atoms.

Any two groups selected from $R^4$, $R^5$, $R^{5'}$, $R^6$, $R^{6'}$, $R^7$, and $R^8$ may be combined so as to form a cyclic structure containing a bicyclo structure or a spiro structure, and may contain one or more heteroatoms optionally selected from oxygen atom, nitrogen atom, or sulfur atom as ring-constituting atom(s).

The ring thus formed may have one or more groups selected from the group consisting of amino group, a halogen atom, hydroxyl group, an alkyl group having 1 to 6 carbon atoms, an alkoxy group having 1 to 6 carbon atoms, and an alkylthio group having 1 to 6 carbon atoms, and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).)

The anti acid-fast bacterial agent wherein Z is a heterocyclic substituent represented by the following formula (4);

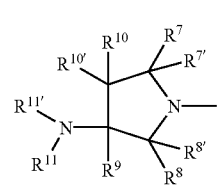

(wherein, $R^{11}$ and $R^{11'}$ each independently represents hydrogen atom or an alkyl group having 1 to 6 carbon atoms,
the alkyl group may have a cyclic structure and may have one or more groups selected from the group consisting of hydroxyl group, a halogen atom, amino group, carbamoyl group, an alkylthio group having 1 to 6 carbon atoms, an alkoxy group having 1 to 6 carbon atoms, an alkylamino group having 1 to 6 carbon atoms, a halogenoalkyl group having 1 to 6 carbon atoms, and an aminoalkyl group having 1 to 6 carbon atoms as substituent(s), $R^9$, $R^{10}$, and $R^{10'}$ each independently represents hydrogen atom, a halogen atom, amino group, hydroxyl group, carbamoyl group, an alkyl group having 1 to 6 carbon atoms, an alkylamino group having 1 to 6 carbon atoms, an aryl group having 6 to 10 carbon atoms, a heteroaryl group (which is a 5- or 6-membered ring and contains 1 to 4 heteroatoms optionally selected from nitrogen atom, oxygen atom, and sulfur atom), an alkoxy group having 1 to 6 carbon atoms, an alkylthio group having 1 to 6 carbon atoms, a halogenoalkyl group having 1 to 6 carbon atoms, or an aminoalkyl group having 1 to 6 carbon atoms, the alkyl group or the alkyl moiety of the alkylamino group, alkoxy group, alkylthio group, halogenoalkyl group, and aminoalkyl group may have a cyclic structure, further, may have one or more groups selected from the group consisting of a halogen atom, an alkyl group having 1 to 6 carbon atoms, and an alkoxy group having 1 to 6 carbon atoms as substituent(s).

The amino moiety of the amino group, aminoalkyl group, and alkylamino group may have one or two alkyl groups having 1 to 6 carbon atoms (the alkyl group may have a cyclic structure, and may have one or more groups selected from the group consisting of hydroxyl group, a halogen atom, an alkylthio group having 1 to 6 carbon atoms, and an alkoxy group having 1 to 6 carbon atoms as substituent(s))(when two alkyl groups are present, they may be the same or different), and the amino moiety may be protected by a protective group.

The aryl group and heteroaryl group may have one or more groups selected from the group consisting of a halogen atom, hydroxyl group, thiol group, amino group, nitro group, cyano group, carboxyl group, carbamoyl group, phenyl group, an alkyl group having 1 to 6 carbon atoms, an alkoxy group having 1 to 6 carbon atoms, an alkylthio group having 1 to 6 carbon atoms, an alkoxycarbonyl group having 2 to 6 carbon atoms, an acyl group having 2 to 5 carbon atoms, and a heteroaryl group (which is a 5- or 6-membered ring and contains 1 to 4 heteroatoms optionally selected from nitrogen atom, oxygen atom, and sulfur atom) as substituent(s), among them, the alkyl group, alkoxy group, alkylthio group, alkoxycarbonyl group, acyl group, phenyl group, and heteroaryl group may have one or more groups selected from the group consisting of a halogen atom, hydroxyl group, an alkoxy group having 1 to 6 carbon atoms, and an alkylthio group having 1 to 6 carbon atoms as substituent(s), and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).

$R^7$, $R^{7'}$, $R^8$, and $R^{8'}$ each independently represents hydrogen atom or an alkyl group having 1 to 6 carbon atoms.

Any two groups selected from the above $R^7$, $R^{7'}$, $R^8$, $R^{8'}$, $R^9$, $R^{10}$, and $R^{10'}$ may be combined so as to form a cyclic structure containing a bicyclo structure or a spiro structure, and may contain one or more heteroatoms optionally selected from oxygen atom, nitrogen atom, or sulfur atom as ring-constituting atom(s).

The ring thus formed may have one or more groups selected from the group consisting of amino group, a halogen atom, hydroxyl group, an alkyl group having 1 to 6 carbon atoms, an alkoxy group having 1 to 6 carbon atoms, and an alkylthio group having 1 to 6 carbon atoms, and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).)

The anti acid-fast bacterial agent wherein Z is a heterocyclic substituent represented by the following formula (5);

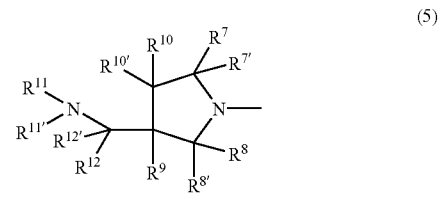

(5)

(wherein, $R^{11}$ and $R^{11'}$ each independently represents hydrogen atom or an alkyl group having 1 to 6 carbon atoms, the alkyl group may have a cyclic structure and may have one or more groups selected from the group consisting of hydroxyl group, a halogen atom, amino group, carbamoyl group, an alkylthio group having 1 to 6 carbon atoms, an alkoxy group having 1 to 6 carbon atoms, an alkylamino group having 1 to 6 carbon atoms, a halogenoalkyl group having 1 to 6 carbon atoms, and an aminoalkyl group having 1 to 6 carbon atoms as substituent(s), $R^9$, $R^{10}$, and $R^{10'}$ each independently represents hydrogen atom, a halogen atom, amino group, hydroxyl group, carbamoyl group, an alkyl group having 1 to 6 carbon atoms, an alkylamino group having 1 to 6 carbon atoms, an aryl group having 6 to 10 carbon atoms, a heteroaryl group (which is a 5- or 6-membered ring and contains 1 to 4 heteroatoms optionally selected from nitrogen atom, oxygen atom, and sulfur atom), an alkoxy group having 1 to 6 carbon atoms, an alkylthio group having 1 to 6 carbon atoms, a halogenoalkyl group having 1 to 6 carbon atoms, or an aminoalkyl group having 1 to 6 carbon atoms, the alkyl group or the alkyl moiety of the alkylamino group, alkoxy group, alkylthio group, halogenoalkyl group, and aminoalkyl group may have a cyclic structure, further, may have one or more groups selected from the group consisting of a halogen atom, an alkyl group having 1 to 6 carbon atoms, and an alkoxy group having 1 to 6 carbon atoms as substituent(s).

The amino moiety of the amino group, aminoalkyl group, and alkylamino group may have one or two alkyl groups having 1 to 6 carbon atoms (the alkyl group may have a cyclic structure, and may have one or more groups selected from the group consisting of hydroxyl group, a halogen atom, an alkylthio group having 1 to 6 carbon atoms, and an alkoxy group having 1 to 6 carbon atoms as substituent(s))(when two alkyl groups are present, they may be the same or different), and the amino moiety may be protected by a protective group.

$R^{12}$ and $R^{12'}$ each independently represents hydrogen atom, an alkyl group having 1 to 6 carbon atoms, an aryl group having 6 to 10 carbon atoms, or a heteroaryl group (which is a 5- or 6-membered ring and contains 1 to 4 heteroatoms optionally selected from nitrogen atom, oxygen atom, and sulfur atom), The aryl group and heteroaryl group may have one or more groups selected from the group consisting of a halogen atom, hydroxyl group, thiol group, amino group, nitro group, cyano group, carboxyl group, carbamoyl group, phenyl group, an alkyl group having 1 to 6 carbon atoms, an alkoxy group having 1 to 6 carbon atoms, an alkylthio group having 1 to 6 carbon atoms, an alkoxycarbonyl group having 2 to 6 carbon atoms, an acyl group having 2 to 5 carbon atoms, and a heteroaryl group (which is a 5- or 6-membered ring and contains 1 to 4 heteroatoms optionally selected from nitrogen atom, oxygen atom, and sulfur atom) as substituent(s), among them, the alkyl group, alkoxy group, alkylthio group, alkoxycarbonyl group, acyl group, phenyl group, and heteroaryl group may have one or more groups selected from the group consisting of a halogen atom, hydroxyl group, an alkoxy group having 1 to 6 carbon atoms, and an alkylthio group having 1 to 6 carbon atoms as substituent(s), and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).

$R^7$, $R^{7'}$, $R^8$, and $R^{8'}$ each independently represents hydrogen atom or an alkyl group having 1 to 6 carbon atoms.

Any two groups selected from $R^7$, $R^{7'}$, $R^8$, $R^{8'}$, $R^9$, $R^{10}$, $R^{10'}$, $R^{12}$, and $R^{12'}$ may be combined so as to form a cyclic structure containing a bicyclo structure or a spiro structure, and may contain one or more heteroatoms optionally selected from oxygen atom, nitrogen atom, or sulfur atom as ring-constituting atom(s).

The ring thus formed may have one or more groups selected from the group consisting of amino group, a halogen atom, hydroxyl group, an alkyl group having 1 to 6 carbon atoms, an alkoxy group having 1 to 6 carbon atoms, and an alkylthio group having 1 to 6 carbon atoms, and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).)

The anti acid-fast bacterial agent wherein Z is a heterocyclic substituent represented by the following formula (6);

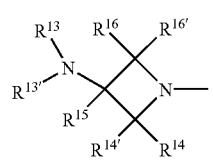

(6)

(wherein, $R^{13}$ and $R^{13'}$ each independently represents hydrogen atom or an alkyl group having 1 to 6 carbon atoms, the alkyl group may have a cyclic structure and may have one or more groups selected from the group consisting of hydroxyl group, a halogen atom, amino group, carbamoyl group, an alkylthio group having 1 to 6 carbon atoms, an alkoxy group having 1 to 6 carbon atoms, an alkylamino group having 1 to 6 carbon atoms, a halogenoalkyl group having 1 to 6 carbon atoms, and an aminoalkyl group having 1 to 6 carbon atoms as substituent(s), $R^{14}$, $R^{15}$ $R^{16}$, and $R^{16'}$ each independently represents hydrogen atom, a halogen atom, amino group, hydroxyl group, carbamoyl group, an alkyl group having 1 to 6 carbon atoms, an alkylamino group having 1 to 6 carbon atoms, an aryl group having 6 to 10 carbon atoms, a heteroaryl group (which is a 5- or 6-membered ring and contains 1 to 4 heteroatoms optionally selected from nitrogen atom, oxygen atom, and sulfur atom), an alkoxy group having 1 to 6 carbon atoms, an alkylthio group having 1 to 6 carbon atoms, a halogenoalkyl group having 1 to 6 carbon atoms, or an aminoalkyl group having 1 to 6 carbon atoms, the alkyl group or the alkyl moiety of the alkylamino group, alkoxy group, alkylthio group, halogenoalkyl group, and aminoalkyl group may have a cyclic structure, further, may have one or more groups selected from the group consisting of a halogen atom, an alkyl group having 1 to 6 carbon atoms, and an alkoxy group having 1 to 6 carbon atoms as substituent(s).

The amino moiety of the amino group, aminoalkyl group, and alkylamino group may have one or two alkyl groups having 1 to 6 carbon atoms (the alkyl group may have a cyclic structure, and may have one or more groups selected from the group consisting of hydroxyl group, a halogen atom, an alkylthio group having 1 to 6 carbon atoms, and an alkoxy group having 1 to 6 carbon atoms as substituent(s))(when two alkyl groups are present, they may be the same or different), and the amino moiety may be protected by a protective group.

The aryl group and heteroaryl group may have one or more groups selected from the group consisting of a halogen atom, hydroxyl group, thiol group, amino group, nitro group, cyano group, carboxyl group, carbamoyl group, phenyl group, an alkyl group having 1 to 6 carbon atoms, an alkoxy group having 1 to 6 carbon atoms, an alkylthio group having 1 to 6 carbon atoms, an alkoxycarbonyl group having 2 to 6 carbon atoms, an acyl group having 2 to 5 carbon atoms, and a heteroaryl group (which is a 5- or 6-membered ring and contains 1 to 4 heteroatoms optionally selected from nitrogen atom, oxygen atom, and sulfur atom) as substituent(s), among them, the alkyl group, alkoxy group, alkylthio group, alkoxycarbonyl group, acyl group, phenyl group, and heteroaryl group may have one or more groups selected from the group consisting of a halogen atom, hydroxyl group, an alkoxy group having 1 to 6 carbon atoms, and an alkylthio group having 1 to 6 carbon atoms as substituent(s), and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).

Any two groups selected from the above $R^{14}$, $R^{14'}$, $R^{15}$, $R^{16}$, and $R^{16'}$ may be combined so as to form a cyclic structure containing a bicyclo structure or a spiro structure, and may contain one or more heteroatoms optionally selected from oxygen atom, nitrogen atom, or sulfur atom as ring-constituting atom(s).

The ring thus formed may have one or more groups selected from the group consisting of amino group, a halogen atom, hydroxyl group, an alkyl group having 1 to 6 carbon atoms, an alkoxy group having 1 to 6 carbon atoms, and an alkylthio group having 1 to 6 carbon atoms, and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).)

The anti acid-fast bacterial agent wherein Z is a heterocyclic substituent represented by the following formula (7);

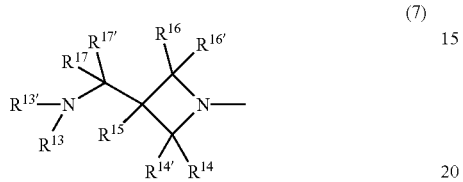

(7)

(wherein, $R^{13}$ and $R^{13'}$ each independently represents hydrogen atom or an alkyl group having 1 to 6 carbon atoms, the alkyl group may have a cyclic structure and may have one or more groups selected from the group consisting of hydroxyl group, a halogen atom, amino group, carbamoyl group, an alkylthio group having 1 to 6 carbon atoms, an alkoxy group having 1 to 6 carbon atoms, an alkylamino group having 1 to 6 carbon atoms, a halogenoalkyl group having 1 to 6 carbon atoms, and an aminoalkyl group having 1 to 6 carbon atoms as substituent(s), $R^{14}$, $R^{15}$, $R^{15'}$, $R^{16}$, and $R^{16'}$ each independently represents hydrogen atom, a halogen atom, amino group, hydroxyl group, carbamoyl group, an alkyl group having 1 to 6 carbon atoms, an alkylamino group having 1 to 6 carbon atoms, an aryl group having 6 to 10 carbon atoms, a heteroaryl group (which is a 5- or 6-membered ring and contains 1 to 4 heteroatoms optionally selected from nitrogen atom, oxygen atom, and sulfur atom), an alkoxy group having 1 to 6 carbon atoms, an alkylthio group having 1 to 6 carbon atoms, a halogenoalkyl group having 1 to 6 carbon atoms, or an aminoalkyl group having 1 to 6 carbon atoms, the alkyl group or the alkyl moiety of the alkylamino group, alkoxy group, alkylthio group, halogenoalkyl group, and aminoalkyl group may have a cyclic structure, further, may have one or more groups selected from the group consisting of a halogen atom, an alkyl group having 1 to 6 carbon atoms, and an alkoxy group having 1 to 6 carbon atoms as substituent(s).

The amino moiety of the amino group, aminoalkyl group, and alkylamino group may have one or two alkyl groups having 1 to 6 carbon atoms (the alkyl group may have a cyclic structure, and may have one or more groups selected from the group consisting of hydroxyl group, a halogen atom, an alkylthio group having 1 to 6 carbon atoms, and an alkoxy group having 1 to 6 carbon atoms as substituent(s))(when two alkyl groups are present, they may be the same or different), and the amino moiety may be protected by a protective group.

$R^{17}$ and $R^{17'}$ each independently represents hydrogen atom, an alkyl group having 1 to 6 carbon atoms, an aryl group having 6 to 10 carbon atoms, or a heteroaryl group (which is a 5- or 6-membered ring and contains 1 to 4 heteroatoms optionally selected from nitrogen atom, oxygen atom, and sulfur atom), The aryl group and heteroaryl group may have one or more groups selected from the group consisting of a halogen atom, hydroxyl group, thiol group, amino group, nitro group, cyano group, carboxyl group, carbamoyl group, phenyl group, an alkyl group having 1 to 6 carbon atoms, an alkoxy group having 1 to 6 carbon atoms, an alkylthio group having 1 to 6 carbon atoms, an alkoxycarbonyl group having 2 to 6 carbon atoms, an acyl group having 2 to 5 carbon atoms, and a heteroaryl group (which is a 5- or 6-membered ring and contains 1 to 4 heteroatoms optionally selected from nitrogen atom, oxygen atom, and sulfur atom) as substituent(s), among them, the alkyl group, alkoxy group, alkylthio group, alkoxycarbonyl group, acyl group, phenyl group, and heteroaryl group may have one or more groups selected from the group consisting of a halogen atom, hydroxyl group, an alkoxy group having 1 to 6 carbon atoms, and an alkylthio group having 1 to 6 carbon atoms as substituent(s), and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).

Any two groups selected from the above $R^{14}$, $R^{14'}$, $R^{15}$, $R^{16}$, $R^{16'}$, $R^{17}$, and $R^{17'}$ may be combined so as to form a cyclic structure containing a bicyclo structure or a spiro structure, and may contain one or more heteroatoms optionally selected from oxygen atom, nitrogen atom, or sulfur atom as ring-constituting atom(s).

The ring thus formed may have one or more groups selected from the group consisting of amino group, a halogen atom, hydroxyl group, an alkyl group having 1 to 6 carbon atoms, an alkoxy group having 1 to 6 carbon atoms, and an alkylthio group having 1 to 6 carbon atoms, and further, the amino group may have one or two groups selected from the group consisting of formyl group, an alkyl group having 1 to 6 carbon atoms, an acyl group having 2 to 5 carbon atoms, and an alkoxycarbonyl group having 2 to 5 carbon atoms as substituent(s).)

The anti acid-fast bacterial agent wherein, in the compound represented by the formula (1), Z is a heterocyclic substituent selected from the following group;

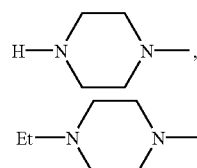

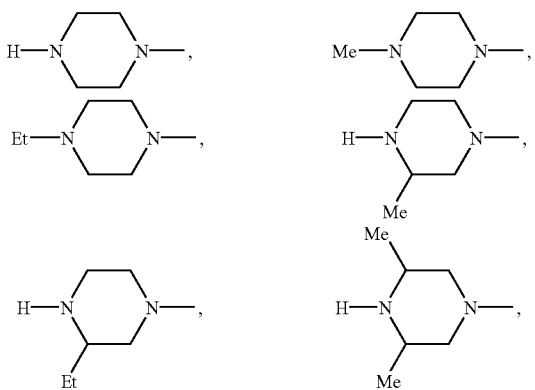

-continued
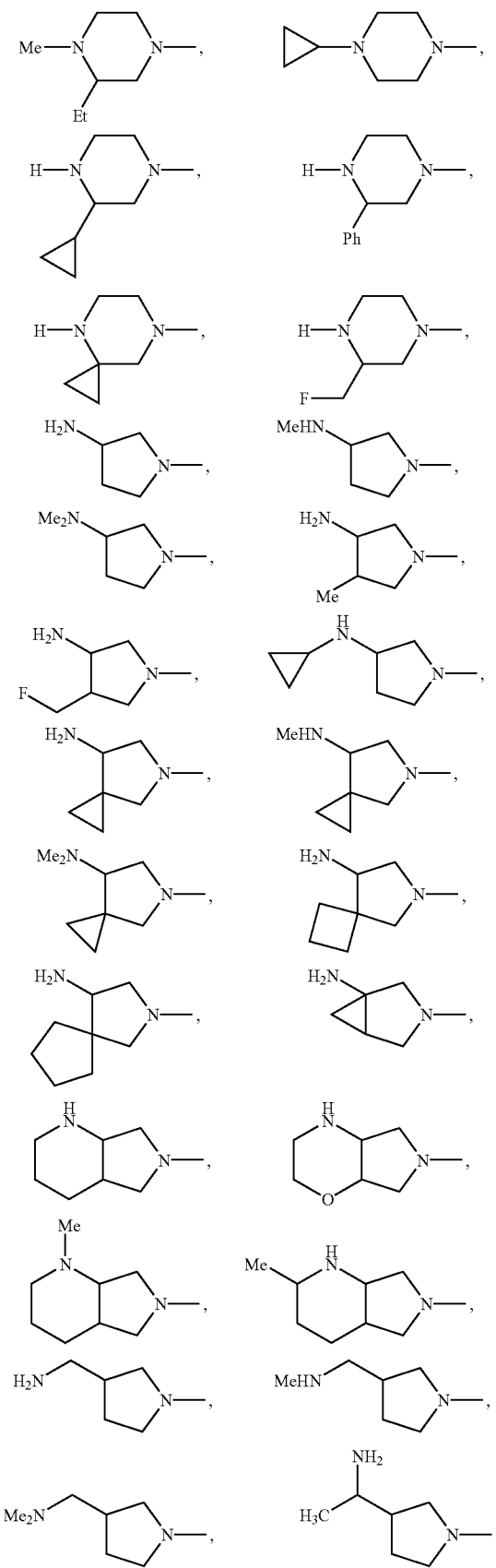
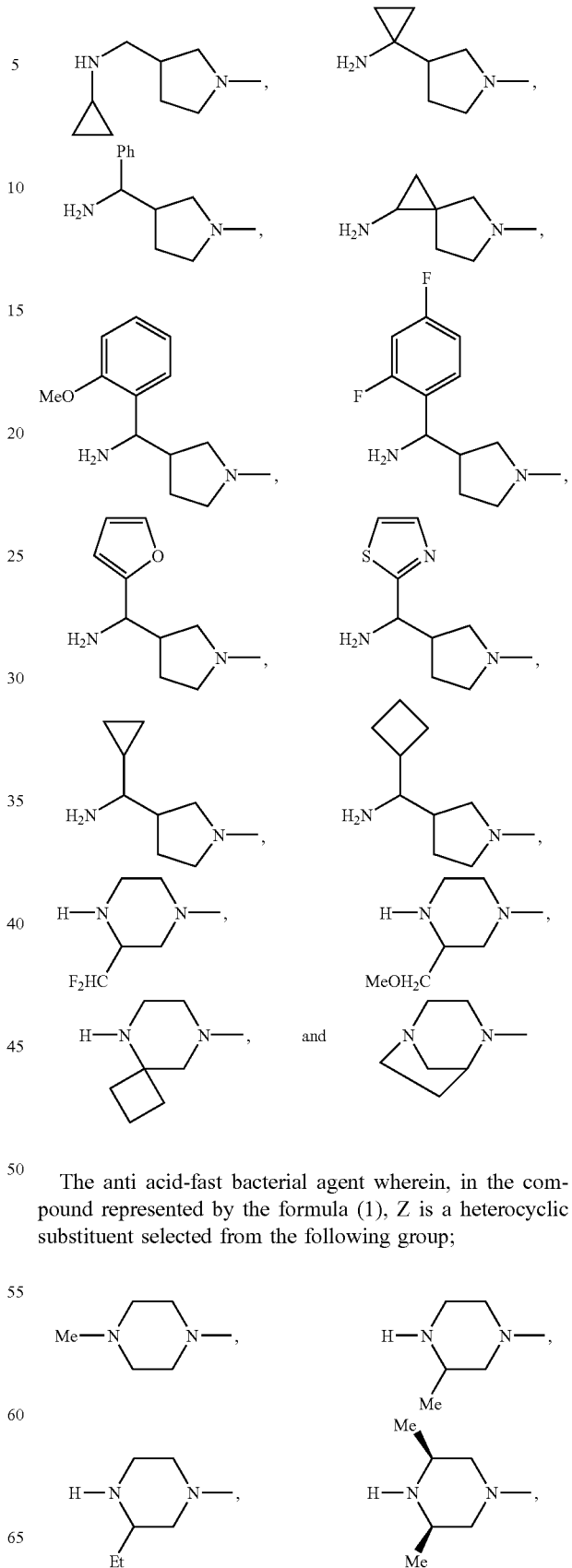
The anti acid-fast bacterial agent wherein, in the compound represented by the formula (1), Z is a heterocyclic substituent selected from the following group;

-continued

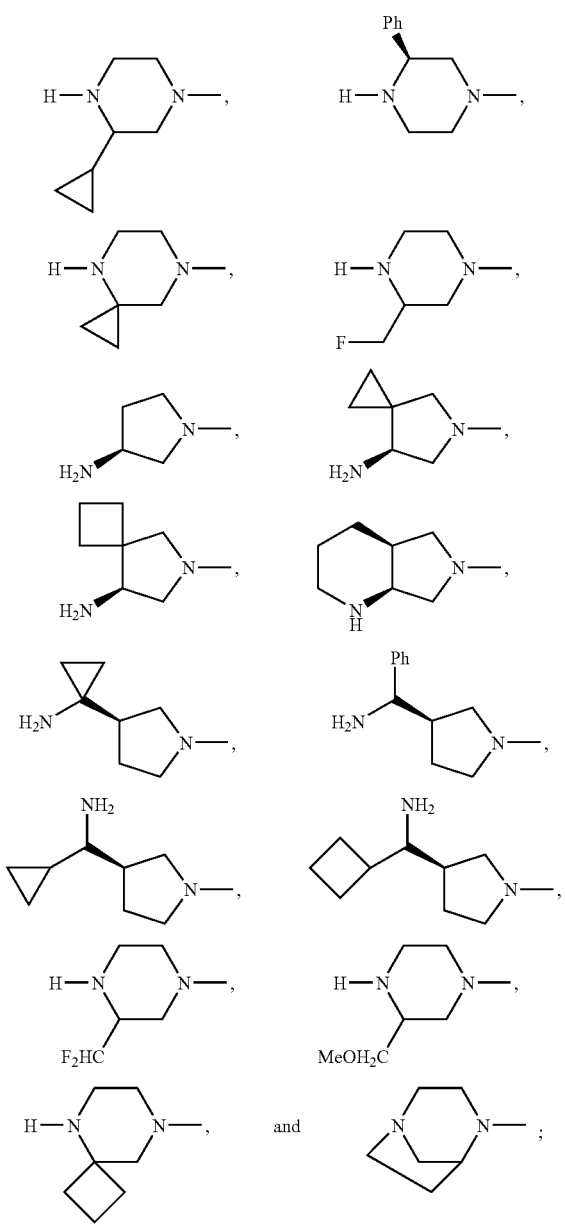

and the like.

Among the compounds represented by the formula (1)

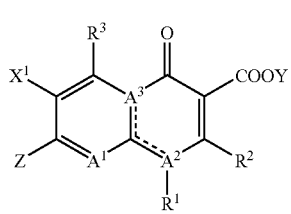
(1)

(wherein, $A^1$, $A^2$, $R^1$, $R^2$, $R^3$, $X^1$, Y and Z are the same as the above definitions.), preferred are those represented by the formula

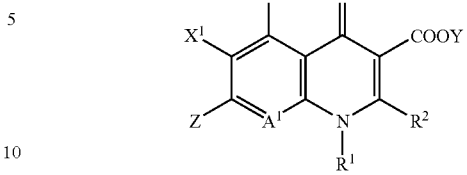

or the formula.

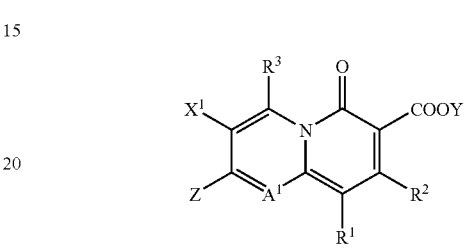

The substituent $R^1$ is an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have substituent(s), an aryl group having 6 to 10 carbon atoms which may have substituent(s), a heteroaryl group which may have substituent(s), an alkoxy group having 1 to 6 carbon atoms, or an alkylamino group having 1 to 6 carbon atoms.

The alkyl group having 1 to 6 carbon atoms is preferably ethyl group. The alkenyl group having 2 to 6 carbon atoms is preferably vinyl group or 1-isopropenyl group. The halogenoalkyl group having 1 to 6 carbon atoms is preferably 2-fluoroethyl group. The cyclic alkyl group having 3 to 6 carbon atoms is preferably cyclopropyl group, and preferred substituent of the cyclic alkyl group is a halogen atom. The halogen atom is preferably fluorine atom.

The aryl group which may have substituent(s) is exemplified by a phenyl group having as substituent(s), 1 to 3 groups selected from the group consisting of a halogen atom such as fluorine atom, chlorine atom, bromine atom, etc., hydroxyl group, amino group, nitro group, an alkyl group having 1 to 6 carbon atoms, an alkoxy group having 1 to 6 carbon atoms, and the like. Preferred are phenyl group, 2-fluorophenyl group, 4-fluorophenyl group, 2,4-difluoro phenyl group, 2-fluoro-4-hydroxyphenyl group, 3-amino-4,6-difluorophenyl group, and 4,6-difluoro-3-methylaminophenyl group.

The heteroaryl group which may have substituent(s) is exemplified by pyridyl group, pyrimidine group, and the like. The substituent on the ring is preferably an alkyl group, a halogen group, or the like. Among them, more preferred is 6-amino-3,5-difluoro-2-pyridyl group.

The alkoxy group having 1 to 6 carbon atoms is preferably methoxy group. The alkylamino group having 1 to 6 carbon atoms is preferably methylamino group.

The substituent $R^1$ is preferably a cyclic alkyl group or a halogenocycloalkyl group. Among them, preferred is cyclopropyl group or 2-halogenocyclopropyl group. The halogen atom is more preferably fluorine atom.

The substituent $R^2$ represents hydrogen atom or an alkylthio group having 1 to 6 carbon atoms, and $R^2$ is preferably hydrogen atom. Also, $R^1$ and $R^2$ may be preferably combined so as to form a cyclic structure with including a part of the mother nucleus (the ring may contain a sulfur atom as a ring-constituting atom, and further, the ring may have an alkyl group having 1 to 6 carbon atoms as a substituent).

The substituent $R^3$ represents hydrogen atom, amino group (which may have one or more groups selected from formyl group, an alkyl group having 1 to 6 carbon atoms, and an acyl group having 2 to 5 carbon atoms as substituent(s)), thiol group, a halogenomethyl group, an alkyl group having 1 to 6 carbon atoms, an alkenyl group having 2 to 6 carbon atoms, an alkynyl group having 2 to 6 carbon atoms, or an alkoxy group having 1 to 6 carbon atoms. Among them, preferred is hydrogen atom, amino group, or an alkyl group having 1 to 6 carbon atoms.

$A^1$ represents nitrogen atom or a partial structure represented by the formula (2)

(2)

(wherein, $X^2$ is the same as the above definition). All of them exhibit the advantages of the invention well but, in the case that $A^1$ is the partial structure represented by the formula (2), $X^2$ is preferably hydrogen atom, a halogen atom, a halogenomethoxy group, an alkyl group having 1 to 6 carbon atoms, or an alkoxy group having 1 to 6 carbon atoms. In addition, $X^2$ may be combined with the above $R^1$ so as to form a cyclic structure with including a part of the mother nucleus, and the ring thus formed preferably contains oxygen atom as a ring-constituting atom, and further, the substituent which the ring may have is preferably methyl group or a halogenomethyl group. And, the halogenomethyl group is preferably monofluoromethyl group.

The substituent $X^1$ represents a halogen atom, hydrogen atom, or amino group. Among them, a halogen atom is preferably fluorine atom.

Y represents hydrogen atom, phenyl group, acetoxymethyl group, pivaloyloxymethyl group, ethoxycarbonyl group, choline group, dimethylaminoethyl group, 5-indanyl group, phthalidinyl group, a 5-alkyl-2-oxo-1,3-dioxol-4-yl-methyl group, 3-acetoxy-2-oxobutyl group, an alkyl group having 1 to 6 carbon atoms, an alkoxymethyl group having 2 to 7 carbon atoms, or a phenylalkyl group which is constituted by an alkylene group having 1 to 6 carbon atoms and phenyl group. Among them, preferred is hydrogen atom.

The substituent Z represents a saturated, partially saturated or unsaturated heterocyclic substituent which is monocyclic, bicyclic, or tricyclic, which may contain one or more heteroatoms selected from the group consisting of nitrogen atom, oxygen atom, and sulfur atom, and which may form a bicyclo structure or a spiro structure. The heterocyclic substituent may be combined with the mother nucleus through any atom constituting the ring, and preferred examples include the following which are combined through a nitrogen atom.

The following formula (3)

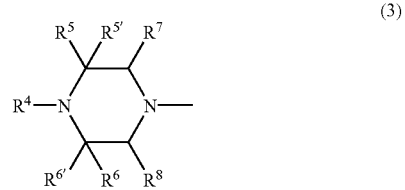

(3)

(wherein, $R^4$, $R^5$, $R^{5'}$, $R^6$, $R^{6'}$, $R^7$, and $R^8$ are the same as the above definitions)

or the following formula (4)

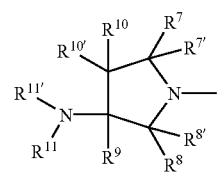

(4)

(wherein, $R^7$, $R^{7'}$, $R^8$, $R^{8'}$, $R^9$, $R^{10}$, $R^{10'}$, $R^{11}$, and $R^{11'}$ are the same as the above definitions)

or the following formula (5)

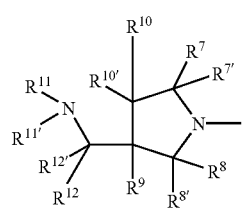

(5)

(wherein, $R^7$, $R^{7'}$, $R^8$, $R^{8'}$, $R^9$, $R^{10}$, $R^{10'}$, $R^{11}$, $R^{11'}$, $R^{12}$, and $R^{12'}$ are the same as the above definitions)

or the following formula (6)

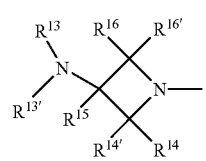

(6)

(wherein, $R^{13}$, $R^{13'}$, $R^{14}$, $R^{14'}$, $R^{15}$, $R^{16}$, and $R^{16'}$ are the same as the above definitions)

or the following formula (7)
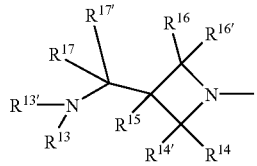
(wherein, $R^{13}$, $R^{13'}$, $R^{14}$, $R^{14'}$, $R^{15}$, $R^{16}$, $R^{16'}$, $R^{17}$, and $R^{17'}$ are the same as the above definitions).
Furthermore, preferred examples include the following groups:
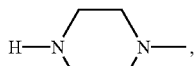 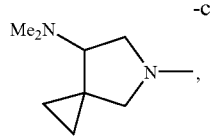 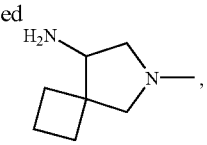
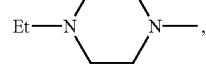 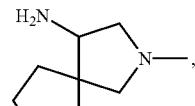 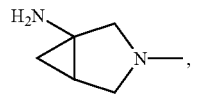
 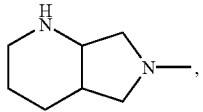 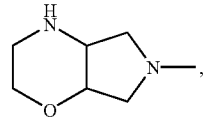
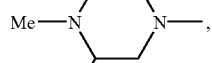 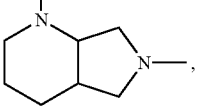 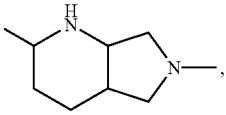
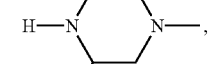 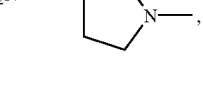 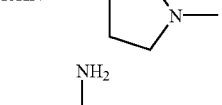
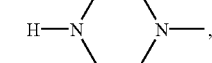  
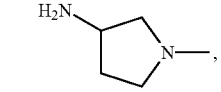 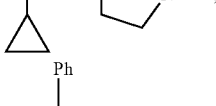 
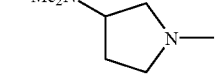 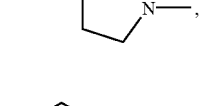 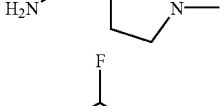
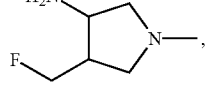 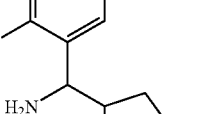 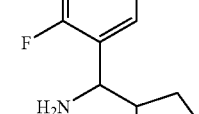
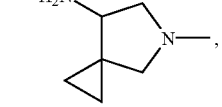 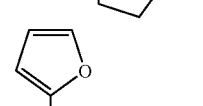 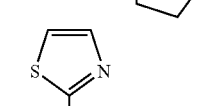
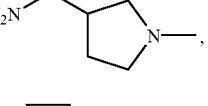 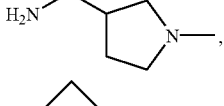
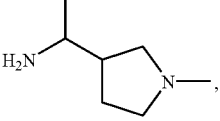 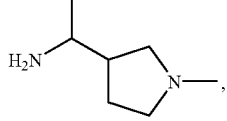

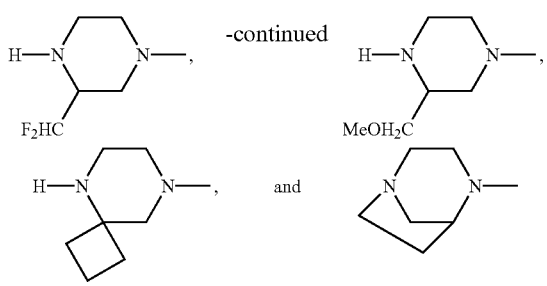

Moreover, more preferred examples include the following groups:

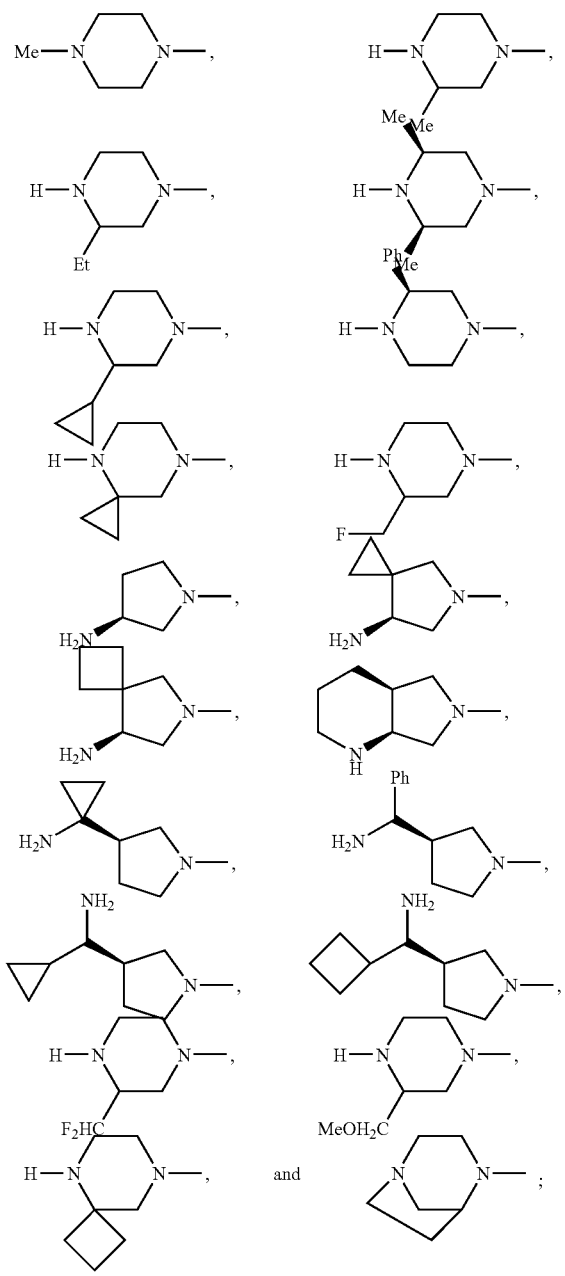

Furthermore, concrete examples of preferred compounds exhibiting the advantages of the invention include the following compounds:

a 6-carboxy-9-fluoro-2,3-dihydro-3-(S)-methyl-7-oxo-7H-pyrido[1,2,3-de][1.4]benzoxazine derivative having Z at the 10-position, an 8-amino-6-carboxy-9-fluoro-2,3-dihydro-3-(S)-methyl-7-oxo-7H-pyrido[1,2,3-de][1.4]benzoxazine derivative having Z at the 10-position, a 3-carboxy-6-fluoro-1-[2-(S)-fluoro-1-(R)-cyclopropyl]-1,4-dihydro-4-oxo-1,8-naphthyridine derivative having Z at the 7-position, a 3-carboxy-8-chloro-6-fluoro-1-[2-(S)-fluoro-1-(R)-cyclopropyl]-1,4-dihydro-4-oxoquinoline derivative having Z at the 7-position, a 3-carboxy-6-fluoro-1-[2-(S)-fluoro-1-(R)-cyclopropyl]-8-methoxy-1,4-dihydro-4-oxoquinoline derivative having Z at the 7-position.

a 3-carboxy-1-[2-(S)-fluoro-1-(R)-cyclopropyl]-8-methoxy-1,4-dihydro-4-oxoquinoline derivative having Z at the 7-position, a 3-carboxy-6-fluoro-1-[2-(S)-fluoro-1-(R)-cyclopropyl]-8-difluoromethoxy-1,4-dihydro-4-oxoquinoline derivative having Z at the 7-position, a 3-carboxy-1-[2-(S)-fluoro-1-(R)-cyclopropyl]-8-difluoromethoxy-1,4-dihydro-4-oxoquinoline derivative having Z at the 7-position, a 3-carboxy-6-fluoro-1-[2-(S)-fluoro-1-(R)-cyclopropyl]-8-methyl-1,4-dihydro-4-oxoquinoline derivative having Z at the 7-position, a 5-amino-3-carboxy-6-fluoro-1-[2-(S)-fluoro-1-(R)-cyclopropyl]-8-methoxy-1,4-dihydro-4-oxoquinoline derivative having Z at the 7-position, a 5-amino-3-carboxy-6-fluoro-1-[2-(S)-fluoro-1-(R)-cyclopropyl]-8-methyl-1,4-dihydro-4-oxoquinoline derivative having Z at the 7-position, a 5-amino-3-carboxy-6,8-difluoro-1-[2-(S)-fluoro-1-(R)-cyclopropyl]-1,4-dihydro-4-oxoquinoline derivative having Z at the 7-position, a 3-carboxy-8-chloro-6-fluoro-1-cyclopropyl-1,4-dihydro-4-oxoquinoline derivative having Z at the 7-position, a 3-carboxy-6-fluoro-1-cyclopropyl-8-methoxy-1,4-dihydro-4-oxoquinoline derivative having Z at the 7-position, a 3-carboxy-1-cyclopropyl-8-methoxy-1,4-dihydro-4-oxoquinoline derivative having Z at the 7-position, a 3-carboxy-6-fluoro-1-cyclopropyl-8-difluoromethoxy-1,4-dihydro-4-oxoquinoline derivative having Z at the 7-position, a 3-carboxy-1-cyclopropyl-8-difluoromethoxy-1,4-dihydro-4-oxoquinoline derivative having Z at the 7-position, a 3-carboxy-6-fluoro-1-cyclopropyl-8-methyl-1,4-dihydro-4-oxoquinoline derivative having Z at the 7-position, a 5-amino-3-carboxy-6-fluoro-1-cyclopropyl-8-methoxy-1,4-dihydro-4-oxoquinoline derivative having Z at the 7-position, a 5-amino-3-carboxy-6-fluoro-1-cyclopropyl-8-methyl-1,4-dihydro-4-oxoquinoline derivative having Z at the 7-position, a 5-amino-3-carboxy-6,8-difluoro-1-cyclopropyl-1,4-dihydro-4-oxoquinoline derivative having Z at the 7-position (wherein, the substituent Z which these derivatives have is the same as the above definition.).

Moreover, concrete examples of more preferred compounds exhibiting the advantages of the invention include the compounds shown in the following table. (in the table, the compounds with number shown in the parentheses are compounds substituted by fluorocyclopropyl group.)

TABLE 1

| Mother Nucleus | | | | |
|---|---|---|---|---|
| Z | Compound 1 (Compound 2) | Compound 5 (Compound 6) | Compound 9 (Compound 10) | Compound 13 |
| | Compound 3 (Compound 4) | Compound 7 (Compound 8) | Compound 11 (Compound 12) | Compound 14 |
| | | (Compound 15) | | |
| | | (Compound 16) | | |

TABLE 1-continued

Mother Nucleus (Compound 17)
(Compound 18)
(Compound 19)
(Compound 22)
(Compound 23)

TABLE 1-continued

Mother Nucleus

| Structure | Structure | Structure | Structure |
|---|---|---|---|
| 8-Cl cipro-type | 8-OMe cipro-type | 8-Me cipro-type | methyl oxazino quinolone |
| (Compound 24) | Compound 25<br>(Compound 26) | | Compound 27 |
| | (Compound 28) | | |

Z

- 2-cyclopropyl-piperazinyl
- 3-phenyl-piperazinyl
- quinuclidinyl-type amine

The compound represented by the formula (1) may be produced according to various methods and the examples are described in Japanese Patent Laid-Open Nos. 95176/1991, 239857/1994, 300416/1995, 333337/1996, etc.

In the case that the compound of the formula (1) according to the invention has a structure where stereoisomers such as enantiomers or diastereomers are present, it is preferred to administer an agent comprising a stereochemically single compound at the administration to human and animals. The "stereochemically single compound" is understood to be not only a compound containing no other enantiomer or diastereomer but also a compound which is thought to be chemically pure. That is, it is understood that the compound may contain other stereoisomer to such an extent that the isomer does not affect physical constants and physiological activity.

Examples of the protective groups usually used for the amino group of the compound according to the invention include alkoxycarbonyl groups such as tert-butoxycarbonyl group, 2,2,2-trichloroethoxycarbonyl group and the like; aralkyloxycarbonyl groups such as benzyloxycarbonyl group, p-methoxybenzyloxycarbonyl group, p-nitrobenzyloxycarbonyl group and the like; acyl groups such as acetyl group, methoxyacetyl group, trifluoroacetyl group, chloroacetyl group, pivaloyl group, formyl group, benzoyl group and the like; alkyl or aralkyl groups such as tert-butyl group, benzyl group, p-nitrobenzyl group, p-methoxybenzyl group, triphenylmethyl group and the like; ethers such as methoxymethyl group, tert-butoxymethyl group, tetrahydropyranyl group, 2,2,2-trichloroethoxymethyl group and the like; substituted silyl groups such as trimethylsilyl group, isopropyldimethylsilyl group, tert-butyldimethylsilyl group, tribenzylsilyl group, tert-butyldiphenylsilyl group and the like.

The compound according to the present invention may be the free form, an acid-addition salt thereof, or an salt of the carboxyl group thereof. Examples of the acid-addition salt include inorganic acid salts such as hydrochloride, sulfate, nitrate, hydrobromide, hydroiodide, phosphate, and the like; and organic acid salts such as methanesulfonate, benzenesulfonate, toluenesulfonate (sulfonates), acetate, citrate, maleate, fumarate, lactate (carboxylates), and the like.

Further, the salt of the carboxyl group may be an organic or inorganic salt and the examples include alkali metal salts such as lithium salt, sodium salt, potassium salt, etc., alkaline earth metal salts such as magnesium salt, calcium salt, etc., ammonium salt, triethylamine salt, N-methylglucamine salt, tris(hydroxymethyl)aminomethane salt, and the like.

Moreover, the free form, acid-addition salt and salt with the carboxyl group of the pyridonecarboxylic acid derivative may exist as a hydrate.

On the other hand, a pyridonecarboxylic acid derivative wherein the carboxylic acid moiety is esterified is useful as a synthetic intermediate or a prodrug. For example, alkyl esters, benzyl esters, alkoxyalkyl esters and phenyl esters are useful as synthesis intermediates.

The ester to be used as the prodrug is an ester which is easily cleaved in the living body to form free carboxylic acid. The examples include acetoxymethyl ester, pivaloyloxymethyl ester, ethoxycarbonyl ester, choline ester, dimethylaminoethyl ester, 5-indanyl ester, and oxoalkyl esters such as phthalidinyl ester, a 5-alkyl-2-oxo-1,3-dioxol-4-yl-methyl ester and 3-acetoxy-2-oxobutyl ester.

In the case that the compound according to the invention is used as human medicines, the dose ranges from 50 mg to 1 g, preferably from 100 mg to 300 mg, per day for adult. The daily dose may be once a day or with dividing into 2 to 4 doses per day. If necessary, the daily dose may sometimes exceed the above-described range.

Examples of the acid-fast bacteria for which the compounds according to the invention are effective include tubercle bacilli such as Mycobacterium tuberculosis, Mycobacterium bovis, and Mycobacterium africanum; and a typical anti-fast bacteria such as Mycobacterium kansasii, Mycobacterium marinum, Mycobacterium scroflaceum, Mycobacterium avium, Mycobacterium intracellulare, Mycobacterium xenopi, Mycobacterium fortuitum, and Mycobacterium chelonae, and the like.

The acid-fast bacteria-infected diseases caused by these pathogens are classified into tuberculosis, a typical acid-fast bacterial diseases and leprosy depending on the infecting bacteria. The Mycobacterium tuberculosis-infected disease is observed at, other than lung, thoracic cavity, trachea/bronchi, lymph node, systemic dissemination, bone joint, meninges, brain, digestive organs (bowels, liver), skin, mammary gland, eye, tympanum, pharynx, urinary tract, male gentile organs, female gentile organs, and the like. Main infected organ of the a typical acid-fast bacterial diseases (non-tuberculous acid-fast bacterial diseases) is lung, and other examples include focal lymphadenitis, dermal soft tissue, bone joint, systemic dissemination type, and the like.

The antibacterial preparation comprising the compound of the invention can be prepared by the conventional preparation methods for various dose forms with selecting an appropriate dose form according to administration route. As the dose forms for the antibacterial preparation comprising the compound of the invention, for example, tablets, powders, granules, capsules, solutions, syrups, elixiers, oily or aqueous suspensions, and the like can be exemplified as the preparations for oral administration.

For the injections, stabilizers, antiseptics, and solubilizing agents may be sometimes used. After the solution which may contain such excipients is put in a container, the solution may be subjected to lyophilization or the like to prepare a solid preparation which can be dissolved on use. One container may contain either a single dose or several doses.

Examples of dose forms for external administration include solutions, suspensions, emulsions, ointments, gels, creams, lotions, sprays, and the like.

Solid preparations may contain pharmaceutically acceptable additives together with the active compound, and the compound may be mixed with, for example, fillers, extenders, binders, disintegrators, dissolution accelerators, wetting agents, lubricants, and the like, if necessary, to prepare aimed preparations.

Liquid preparations include solutions, suspensions, emulsions, and the like. They may sometimes contain suspension stabilizers, emulsifiers, and the like as the additives.

Methods for administering the compound of the invention to animals may be, for example, a method of administering it orally either directly or as admixture with feedstuff, a method of preparing its solution and then administering it orally either directly or as admixture with water or feedstuff, or a method of administering it by injection.

As preparations for administering the compound of the invention to animals, it can be formulated into powders, fine granules, solubilized powders, syrups, solutions, or injections, by conventional preparation methods in this technical field.

Formulation Examples are shown in Table 2.

TABLE 2

| Formulation Example 1 (Capsule) | |
| --- | --- |
| Compound of the invention | 100.0 mg |
| Corn starch | 23.0 mg |
| CMC calcium | 22.5 mg |
| Hydroxymethyl cellulose | 3.0 mg |
| Magnesium stearate | 1.5 mg |
| total | 150.0 mg |
| Formulation Example 2 (Solution) | |
| Compound of the invention | 1 to 10 g |
| Acetic acid or sodium hydroxide | 0.5 to 2 g |
| Ethyl p-hydroxybenzoate | 0.1 g |
| Purified water | 87.9 to 98.4 g |
| total | 100 g |
| Formulation Example 3 (Powder for Admixture with Feedstuff) | |
| Compound of the invention | 1 to 10 g |
| Corn starch | 98.5 to 89.5 g |
| Light anhydrous silicic acid | 0.5 g |
| total | 100 g |

BEST MODE FOR CARRYING OUT THE INVENTION

EXAMPLES

The following will explain the present invention in detail by way of Examples and Reference Examples, but it should be understood that the present invention is not limited thereto.

Reference Example 1

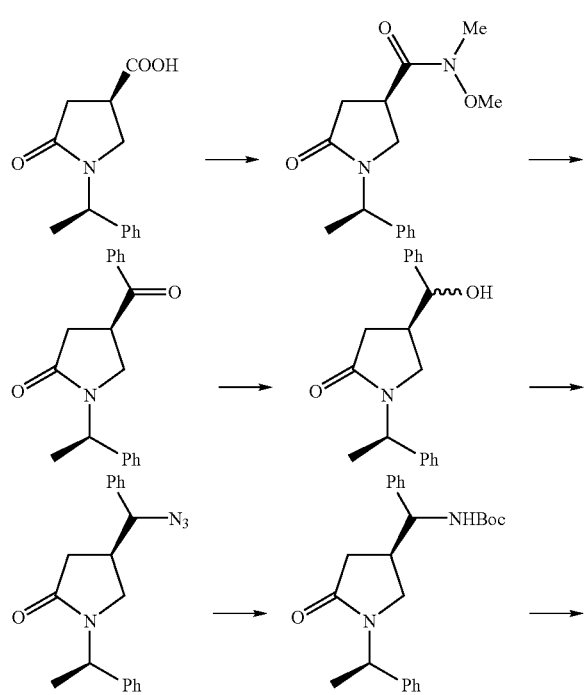

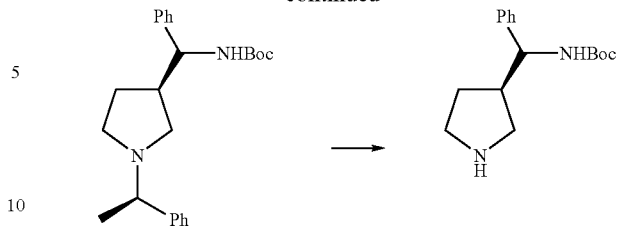

Reference Example 1-1

N-Methyl-N-methoxy-1-[1-(R)-phenylethyl]-5-oxopyrrolidine-3-(R)-carboxamide

To a dichloromethane solution (200 ml) of 1-[1-(R)-phenylethyl]-5-oxopyrrolidine-3-(R)-carboxylic acid (11.66 g, 0.05 mol) were added oxalyl chloride (6.54 ml, 0.075 mol) and dimethylformamide (3 drops) under ice cooling, followed by stirring at room temperature overnight. After removal of the solvent under reduced pressure, toluene (100 ml) was added thereto and the solvent was again removed under reduced pressure. To the residue were added dichloromethane (200 ml) and N,O-methylhydroxylamine hydrochloride (5.47 g, 0.055 mol), and then a dichloromethane solution (50 ml) of triethylamine (17.4 ml, 0.125 mol) was added thereto under ice cooling and stirring over a period of 15 minutes. After stirring under ice cooling for 30 minutes, the mixture was stirred at room temperature for 3 hours. The reaction solution was washed with 10% citric acid aqueous solution (100 ml), water (100 ml) and saturated sodium hydrogen carbonate aqueous solution (100 ml), successively, and then dried over anhydrous sodium sulfate. After removal of the solvent under reduced pressure, the residue was subjected to silica gel column chromatography. Elution with chloroform/methanol of 50/1 to 20/1 afforded the title compound (11.32 g, 82%) as a brown oil.

$^1$H-NMR (400 MHz, CDCl$_3$) δ: 1.54 (3H, d, J=6.84 Hz), 2.65 (1H, dd, J=9.77, 7.09 Hz), 2.77 (1H, dd, J=8.79, 7.09 Hz), 3.12–3.18 (1H, m), 3.20 (3H, s), 3.37–3.48 (1H, m), 3.55–3.64 (1H, m), 3.65 (3H, s), 5.50 (1H, q, J=6.84 Hz), 7.28–7.37 (5H, m).

Reference Example 1-2

4-(R)-Phenylcarbonyl-1-[1-(R)-phenylethyl]-2-pyrrolidone

Under a nitrogen atmosphere, phenylmagnesium bromide (3N diethyl ether solution, 15 ml) was added dropwise to a tetrahydrofuran solution (50 ml) of N-methyl-N-methoxy-1-[1-(R)-phenylethyl]-5-oxopyrrolidine-3-(R)-carboxamide (2.49 g, 9.0 mmol), followed by stirring at room temperature for 30 minutes. To the reaction solution was added 1 mol/l hydrochloric acid (50 ml) under ice cooling and the mixture was extracted with ethyl acetate (8 ml×2). The organic layer was washed with saturated saline (100 ml) and dried over anhydrous sodium sulfate. After removal of the solvent under reduced pressure, the residue was subjected to silica gel column chromatography. Elution with n-hexane/ethyl acetate (1/1) afforded the title compound (2.36 g, 89%) as a pale yellow oil.

$^1$H-NMR (400 MHz, CDCl$_3$) δ: 1.55 (3H, d, J=6.83 Hz), 2.79 (1H, dd, J=17.09, 9.77 Hz), 2.81 (1H, dd, J=17.09, 7.81

Hz), 3.23 (1H, dd, J=9.76, 8.79 Hz), 3.71 (1H, dd, J=9.76, 6.35 Hz), 3.97–4.05 (1H, m), 5.54 (1H, q, J=6.83 Hz), 7.27–7.38 (5H, m), 7.42–7.50 (2H, m), 7.55–7.61 (1H, m), 7.88–7.90 (2H, m).

Reference Example 1-3

4-(R)-[1-Hydroxy-1-phenylmethyl]-1-[1-(R)-phenylethyl]-2-pyrrolidone [F1], [F2]

To an absolute ethanol (40 ml) solution of 4-(R)-phenylcarbonyl-1-[1-(R)-phenylethyl]-2-pyrrolidone (2.17 g, 7.40 mmol) was added sodium borohydride (280 mg) under ice cooling, followed by stirring at the same temperature for 1 hour. To the reaction solution was added 10% citric acid (50 ml) under ice cooling, and then the ethanol was removed under reduced pressure. The residue was extracted with chloroform (80 ml×2) and, after washing with saturated saline (100 ml), the organic layer was dried over anhydrous sodium sulfate. After removal of the solvent under reduced pressure, the residue was subjected to silica gel column chromatography. Elution with eluents of n-hexane/ethyl acetate (1/3) to ethyl acetate (100%) afforded the low polar title compound having low polarity [F1] (892 mg, 41%) and the title compound having high polarity [F2] (1.163 g, 53%) as pale yellow oils.

[F1];
$^1$H-NMR (400 MHz, CDCl$_3$) δ: 1.46 (3H, d, J=6.84 Hz), 2.03–2.14 (2H, m), 2.44–2.54 (1H, m), 3.05–3.09 (1H, m), 3.36–3.40 (1H, m), 3.47 (1H, brs), 4.45 (1H, d, J=7.81 Hz), 5.38 (1H, q, J=6.84 Hz), 7.22–7.31 (10H, m).

[F2];
$^1$H-NMR (400 MHz, CDCl$_3$) δ: 1.37 (3H, d, J=7.32 Hz), 2.26–2.32 (1H, m), 2.40–2.55 (2H, m), 2.73–2.77 (1H, m), 3.00–3.04 (1H, m), 4.32 (1H, brs), 4.42 (1H, d, J=6.8 Hz), 5.33 (1H, q, J=7.32 Hz), 7.15–7.27 (10H, m).

Reference Example 1-4

4-(R)-[1-Azido-1-phenylmethyl]-1-[1-(R)-phenylethyl]-2-pyrrolidone [F1], [F2]

Under ice cooling, triethylamine (0.46 ml) and methanesulfonyl chloride (217 μl, 2.80 mmol) were added to a dichloromethane (10 ml) solution of 4-(R)-[1-hydroxy-1-phenylmethyl]-1-[1-(R)-phenylethyl]-2-pyrrolidone [F1] (738 mg, 2.50 mmol), followed by stirring at the same temperature for 1 hour. To the reaction solution was added 10% citric acid (20 ml) under ice cooling, and the mixture was extracted with chloroform (30 ml×2). After washing with saturated saline (100 ml), the organic layer was dried over anhydrous sodium sulfate. The solvent was removed under reduced pressure, and the residue was dissolved in N,N-dimethylformamide (10 ml). Then, sodium azide (488 mg, 7.50 mmol) was added thereto, followed by stirring at 60° C. for 1.5 hours. After cooling on standing, water (50 ml) was added to the reaction solution and the resulting mixture was extracted with ethyl acetate (70 ml×3). The organic layer was washed with saturated saline (150 ml) and dried over anhydrous sodium sulfate. After removal of the solvent under reduced pressure, the residue was subjected to silica gel column chromatography. Elution with n-hexane/ethyl acetate (3/2) afforded the title compound (701 mg, 87%) as a colorless oil.

The same reaction was applied to 4-(R)-[1-hydroxy-1-phenylmethyl]-1-[1-(R)-phenylethyl]-2-pyrrolidone [F2] (77%).

[F1];
$^1$H-NMR (400 MHz, CDCl$_3$) δ: 1.46 (3H, d, J=7.32 Hz), 2.53–2.66 (3H, m), 2.82 (1H, dd, J=9.76, 7.81 Hz), 2.94 (1H, dd, J=9.76, 5.86 Hz), 4.37 (1H, d, J=7.81 Hz), 5.47 (1H, q, J=7.32 Hz), 7.21–7.42 (10H, m).

[F2];
$^1$H-NMR (400 MHz, CDCl$_3$) δ: 1.54 (3H, d, J=7.33 Hz), 2.14 (1H, dd, J=17.09, 7.81 Hz), 2.26 (1H, dd, J=17.09, 8.78 Hz), 2.55–2.65 (1H, m), 3.14 (1H, dd, J=10.26, 7.81 Hz), 3.32 (1H, dd, J=10.26, 6.34 Hz), 4.36 (1H, d, J=9.28 Hz), 5.49 (1H, q, J=7.33 Hz), 7.26–7.43 (10H, m).

Reference Example 1-5

4-(R)-[1-tert-Butoxycarbonylamino-1-phenylmethyl]-1-[1-(R)-phenylethyl]-2-pyrrolidone [F1], [F2]

To an ethanol (30 ml) solution of 4-(R)-[1-azido-1-phenylmethyl]-1-[1-(R)-phenylethyl]-2-pyrrolidone [F1] (641 mg, 2.0 mmol) was added a 10% palladium-carbon catalyst (water content 53.8%, 600 mg) and catalytic hydrogenation was out at room temperature at normal pressure for 6 hours. The reaction solution was filtered and the solvent was removed under reduced pressure. The residue was dissolved in dichloromethane (20 ml) and di-tert-butyl dicarbonate (655 mg) and triethylamine (560 μl) were added thereto, followed by stirring at room temperature for 13 hours. Chloroform (50 ml) was added to the reaction solution, the resulting mixture was washed with 10% citric acid (8 ml) and water (8 ml), and then the organic layer was dried over anhydrous sodium sulfate. After removal of the solvent under reduced pressure, the residue was subjected to silica gel column chromatography. Elution with n-hexane/ethyl acetate of from 1/1 to 2/3 afforded the title compound (629 mg, 80%) as colorless crystals.

The same reaction was applied to 4-(R)-[1-azido-1-phenylmethyl]-1-[1-(R)-phenylethyl]-2-pyrrolidone [F2] (76%).

[F1];
$^1$H-NMR (400 MHz, CDCl$_3$) δ: 1.41 (9H, s), 1.46 (3H, d, J=7.32 Hz), 2.47–2.76 (3H, m), 2.76–2.89 (1H, m), 2.95–3.08 (1H, m), 4.62–4.73 (1H, m), 4.99–5.11 (1H, m), 5.47 (1H, q, J=7.32 Hz), 7.20–7.34 (10H, m).

[F2];
$^1$H-NMR (400 MHz, CDCl$_3$) δ: 1.37 (9H, s), 1.51 (3H, d, J=7.32 Hz), 2.08–2.26 (2H, m), 2.52–2.65 (1H, m), 3.06–3.18 (1H, m), 3.24–3.32 (1H, m), 4.52–4.66 (1H, m), 5.01–5.11 (1H, m), 5.47 (1H, q, J=7.32 Hz), 7.19–7.35 (10H, m).

Reference Example 1-6

3-(R)-[1-tert-Butoxycarbonylamino-1-phenylmethyl]-1-[1-(R)-phenylethyl]pyrrolidine [F1]

Under a nitrogen atmosphere, 1 mol/l borane-tetrahydrofuran complex (4.6 ml) was added dropwise to a tetrahydrofuran solution (10 ml) of 4-(R)-[1-tert-butoxycarbonylamino-1-phenylmethyl]-1-[1-(R)-phenylethyl]-2-pyrrolidone [F1] (600 mg, 1.52 mmol) under ice cooling, followed by stirring at room temperature for 13 hours. After removal of the solvent under reduced pressure, 80% water-containing ethanol (15 ml) and triethylamine (3 ml) were added to the residue and the mixture was heated under reflux for 5 hours. After cooling on standing, the solvent was removed under reduced pressure and chloroform (30 ml) was added to the residue. The solution was washed with water (10 ml) and saturated saline (10 ml) and dried over anhydrous sodium sulfate. After removal of the solvent under reduced pressure, the residue was subjected to silica gel column chromatography. Elution with chloroform/methanol (20/1) afforded the title compound (510 mg, 88%) as colorless crystals.

The same reaction was applied to 4-(R)-[1-tert-butoxycarbonylamino-1-phenylmethyl]-1-[1-(R)-phenylethyl]-2-pyrrolidone [F2] (86%).

[F1];
$^1$H-NMR (400 MHz, CDCl$_3$) δ: 1.34 (3H, d, J=6.35 Hz), 1.47 (9H, s), 1.60–1.78 (2H, m), 2.18–2.39 (3H, m), 2.42–2.54 (1H, m), 2.83–2.95 (1H, m), 3.11 (1H, q, J=6.35 Hz), 4.47–4.57 (1H, m), 6.06–6.18 (1H, m), 7.16–7.33 (10H, m).

[F2];
$^1$H-NMR (400 MHz, CDCl$_3$) δ: 1.41 (3H, d, J=6.35 Hz), 1.46 (9H, s), 1.67–1.78 (1H, m), 1.89–2.02 (1H, m), 2.04–2.17 (1H, m), 2.17–2.28 (1H, m), 2.37–2.50 (2H, m), 3.01–3.19 (2H, m), 4.48–4.58 (1H, m), 6.62–6.73 (1H, m), 7.07–7.34 (10H, m).

Reference Example 1-7

3-(R)-[1-tert-Butoxycarbonylamino-1-phenylmethyl] pyrrolidine [F1]

To an ethanol (20 ml) solution of 3-(R)-[1-tert-butoxycarbonylamino-1-phenylmethyl]-1-[1-(R)-phenylethyl]pyrrolidine [F1] (495 mg, 1.30 mmol) was added a 10% palladium-carbon catalyst (water content 53.8%, 500 mg) and catalytic hydrogenation was carried out under heating at an outer temperature of 50° C. at normal pressure for 4 hours. The reaction solution was filtered and the solvent was removed under reduced pressure to obtain a crude product of the title compound (359 mg, quantitative) as colorless crystals.

The same reaction was applied to 3-(R)-[1-tert-butoxycarbonylamino-1-phenylmethyl]-1-[1-(R)-phenylethyl]pyrrolidine [F2] (quantitative).

Reference Example 2

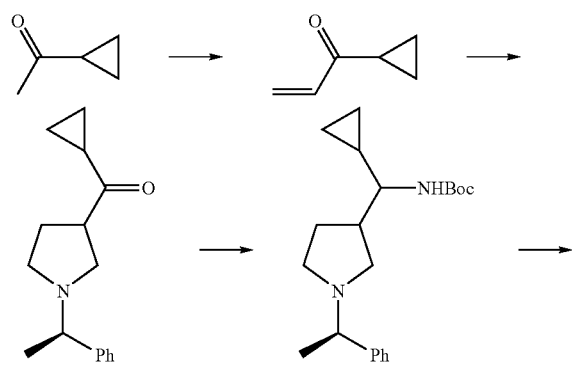

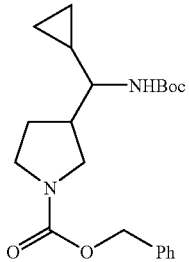

Reference Example 2-1

1-Cyclopropyl-2-propen-1-one

Under a nitrogen stream, cyclopropyl methyl ketone (6.33 g, 75.2 mmol) was dissolved in anhydrous tetrahydrofuran (75 ml). Under stirring and ice cooling, thereto was added dropwise a solution prepared by dissolving N-methylanilinium trifluoroacetate (25.0 g, 113 mmol) in 37% formaldehyde aqueous solution (10.2 ml) under ice cooling. After the addition, the reaction solution was heated under reflux for 7 hours. After cooling on standing, diethyl ether (100 ml) was added to the reaction solution and the resulting mixture was stirred. The organic layer was separated and the aqueous layer was extracted with diethyl ether (50 ml). Under ice cooling, saturated sodium bicarbonate aqueous solution (100 ml) was gradually added to the combined organic layer and, after stirring, the organic layer was separated. The separated organic layer was washed with saturated saline (100 ml). The layer was dried over anhydrous sodium sulfate and, after filtration, the filtrate was concentrated under a reduced pressure of 150 mmHg to a weight of 8.01 g so as to obtain a yellow oil containing the title compound. This product was used in the next reaction without purification.

$^1$H-NMR (400 MHz, CDCl$_3$) δ: 0.90–0.96 (2H, m), 1.08–1.13 (2H, m), 2.14–2.25 (1H, m), 5.82 (1H, dd, J=10.74, 1.47 Hz), 6.29 (1H, dd, J=17.57, 1.47 Hz), 6.47 (1H, dd, J=17.57, 10.74 Hz)

Reference Example 2-2

Cyclopropyl [1-[1-(R)-phenylethyl]pyrrolidin-3-yl] ketone

In dry dichloroethane (350 ml) was dissolved the product (8.01 g) containing 1-cyclopropyl-2-propen-1-one described in Reference Example 2-1 and N-(n-butoxymethyl)-N-[1-(R)-phenylethyl]trimethylsilylmethylamine (23.2 g, 79.9 mmol), followed by dropwise addition of trifluoroacetic acid (500 µl). After stirring at room temperature for 12 hours, the reaction solution was washed with saturated sodium bicarbonate (100 ml) and then saturated saline (100 ml). The solution was dried over anhydrous sodium sulfate and, after filtration, the filtrate was concentrated under reduced pressure. The resulting residue was subjected to flash silica gel chromatography to obtain the title compound (9.08 g, 49.6%) as a colorless oil from the fraction eluted with n-hexane/ethyl acetate=2/1. By the way, this product was obtained as a 1:1 diastereomer mixture.

$^1$H-NMR (400 MHz, CDCl$_3$) δ: 0.83–0.88 (2H, m), 0.99–1.02 (2H, m), 1.38 (3H×1/2, d, J=2.93 Hz), 1.40

(3H×1/2, d, J=2.44 Hz), 1.62–1.76 (1H, m), 1.90–2.17 (2H, m), 2.35–2.93 (4H, m), 3.22–3.26 (2H, m), 7.23–7.34 (5H, m)

Reference Example 2-3

3-[1-(tert-Butoxycarbonyl)amino-1-cyclopropyl]methyl-1-[1-(R)-phenylethyl]pyrrolidine Cyclopropyl [1-[1-(R)-phenylethyl]pyrrolidin-3-yl] ketone (1.563 g, 7.793 mol) was dissolved in absolute methanol (25 ml). Thereto were added ammonium acetate (5.236 g, 67.93 mmol), sodium cyanoborohydride (435.2 mg, 6.925 mmol) and powdered molecular sieves 4A (1.86 g), followed by stirring at room temperature for 16 hours under a nitrogen stream. The reaction solution was filtered through celite and then the solvent was removed under reduced pressure. The residue was dissolved in dichloromethane (100 ml), and the solution was washed with saturated sodium bicarbonate (50 ml) and then saturated saline (50 ml), followed by drying over anhydrous sodium sulfate. After filtration, the solvent was removed under reduced pressure. The resulting residue was dissolved in dry dichloromethane (25 ml) and then a dichloromethane (5 ml) solution of di-tert-butyl dicarbonate (2.225 g, 10.19 mmol) was added dropwise thereto under ice cooling. The reaction solution was stirred at room temperature for 2 hours, and then concentrated under reduced pressure. The resulting residue was subjected to flash silica gel chromatography to obtain the title compound (1.299 g, 55.5%) as a colorless oil from the fraction eluted with chloroform/methanol=10/1. By the way, this product was obtained as a mixture of four kinds of optical isomers.

$^1$H-NMR (400 MHz, CDCl$_3$) δ: 0.20–0.30, 0.35–0.52, 0.68–0.78 (4H, m), 1.36 (3H×1/4, d, J=5.86 Hz), 1.39 (3H×3/4, d, J=5.86 Hz), 1.43 9H×1/4, s), 1.45 (9 H×3/4, s), 1.61–1.74 (1H, m), 2.25–2.76, 2.80–3.07, 3.18–3.26 (9H, m), 5.28 (1H, brs), 7.23–7.34 (5H, m)

Reference Example 2-4

1-Benzyloxycarbonyl-3-[1-(tert-butoxycarbonyl)amino-1-cyclopropyl]methylpyrrolidine
(F1, F2, F3, F4)

In dry dichloromethane (20 ml) was dissolved 3-[1-(tert-butoxycarbonyl)amino-1-cyclopropyl]methyl-1-[1-(R)-phenylethyl]pyrrolidine (1.234 g, 3.582 mmol). Under ice cooling, benzyl chloroformate (1278 µl, 8.955 mmol) was added thereto. After stirring at room temperature for 8 hours, the reaction solution was concentrated under reduced pressure. The resulting residue was subjected to flash silica gel chromatography to obtain the title compound (959 mg, 71.5%) as a colorless oil from the fraction eluted with n-hexane/ethyl acetate=2/1.

Then, this product was subjected to preparative HPLC using a chiral column to separate and purify four kinds of optical isomers F1, F2, F3, and F4.
Separation conditions for HPLC;
Column: CHIRALPAKAD (Daicel Chemical Industries, Ltd.), 2 cm×25 cm
Mobile phase: n-hexane/2-propanol=80:20 (v/v)
Flow rate: 5.0 ml/minute
Temperature: room temperature
Detection: UV (254 nm)
Retention time of each optical isomer
F1: 18 minutes; F2: 23 minutes; F3: 26 minutes; F4: 30 minutes Isomer F1: colorless amorphous, 229 mg (17.0%);
$^1$H-NMR (400 MHz, CDCl$_3$) δ: 0.27–0.32 (2H, m), 0.41–0.45 (1H, m), 0.54–0.61 (1H, m), 0.72–0.79 (1H, m), 1.43 (9H, s), 1.66–1.78 (1H, m), 1.99–2.08 (1H, m), 2.30–2.36 (1H, m), 2.90–3.03 (1H, m), 3.12–3.26 (1H, m), 3.28–3.36 (1H, m), 3.49–3.72 (2H, m), 4.50 (1H, brs), 5.13 (2H, s), 7.30–7.37 (5H, m)

Isomer F2: colorless amorphous, 96 mg (7.2%);
$^1$H-NMR (400 MHz, CDCl$_3$) δ: 0.29–0.37 (2H, m), 0.40–0.45 (1H, m), 0.57–0.62 (1H, m), 0.76–0.79 (1H, m), 1.43 (9H, s), 1.68–1.78 (1H, m), 2.04–2.09 (1H, m), 2.36–2.40 (1H, m), 2.95–3.09 (1H, m), 3.16 (1H, t, J=10.74 Hz), 3.31–3.39 (1H, m), 3.54–3.68 (2H, m), 4.47 (1H, brs), 5.13 (2H, s), 7.29–7.37 (5H, m)

Isomer F3: colorless amorphous, 140 mg (10.4%);
$^1$H-NMR (400 MHz, CDCl$_3$) δ: 0.27–0.39 (2H, m), 0.41–0.45 (1H, m), 0.54–0.62 (1H, m), 0.72–0.80 (1H, m), 1.43 (9H, s), 1.66–1.79 (1H, m), 2.04–2.09 (1H, m), 2.37–2.40 (1H, m), 2.95–3.08 (1H, m), 3.16 (1H, t, J=10.74 Hz), 3.32–3.39 (1H, m), 3.54–3.68 (2H, m), 4.48 (1H, brs), 5.13 (2H, s), 7.30–7.37 (5H, m)

Isomer F4: colorless amorphous, 296 mg (22.1%);
$^1$H-NMR (400 MHz, CDCl$_3$) δ: 0.27–0.33 (2H, m), 0.41–0.45 (1H, m), 0.54–0.62 (1H, m), 0.72–0.80 (1H, m), 1.43 (9H, s), 1.68–1.78 (1H, m), 1.99–2.09 (1H, m), 2.29–2.39 (1H, m), 2.90–3.03 (1H, m), 3.12–3.26 (1H, m), 3.28–3.37 (1H, m), 3.49–3.73 (2H, m), 4.50 (1H, brs), 5.13 (2H, s), 7.30–7.37 (5H, m)

From the analysis of the above $^1$H-NMR data, among four kinds of the optical isomers, it is revealed that relationship of F1 and F4 and that of F2 and F3 are enantiomeric ones, respectively.

Reference Example 3

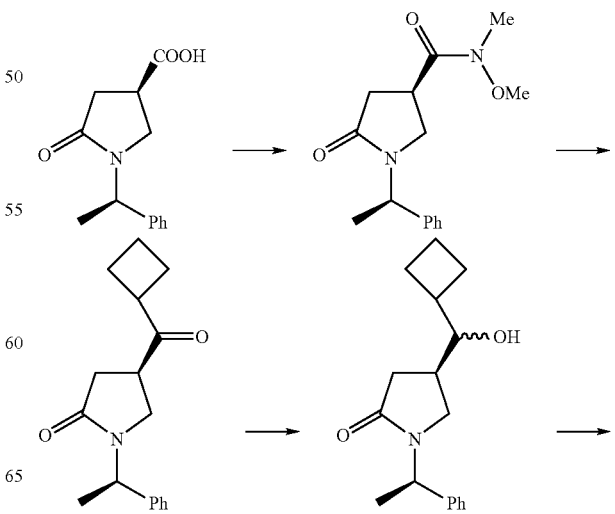

-continued

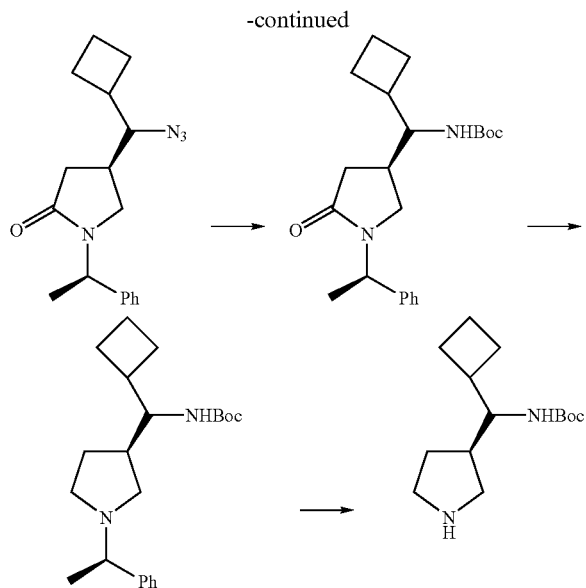

Reference Example 3-1

1-[1-(R)-Phenylethyl]-5-oxopyrrolidine-3-(R)—(N-methyl-N-methoxy)carboxamide

To a dichloromethane solution (200 ml) of 1-[1-(R)-phenylethyl]-5-oxopyrrolidine-3-(R)-carboxylic acid (11.7 g, 50.0 mmol) were added oxalyl chloride (6.54 ml, 75.0 mmol) and dimethylformamide (3 drops) under ice cooling, followed by stirring at room temperature overnight. After removal of the solvent under reduced pressure, toluene (100 ml) was added thereto and the solvent was again removed under reduced pressure. To the residue were added dichloromethane (200 ml) and N,O-methylhydroxylamine hydrochloride (5.47 g, 55.5 mmol), and then a dichloromethane solution (50 ml) of triethylamine (17.4 ml, 125 mmol) was added thereto under ice cooling and stirring over a period of 15 minutes. After stirring under ice cooling for 30 minutes, the mixture was stirred at room temperature for 3 hours. The reaction solution was washed with 10% citric acid aqueous solution (100 ml), water (100 ml) and saturated sodium hydrogen carbonate aqueous solution (100 ml), successively, and then dried over anhydrous sodium sulfate. After removal of the solvent under reduced pressure, the residue was subjected to silica gel column chromatography to obtain the title compound (11.3 g, 82%) as a brown oil from the fraction eluted with chloroform/methanol of 50/1 to 20/1.

$^1$H-NMR (400 MHz, CDCl$_3$) δ: 1.54 (3H, d, J=6.84 Hz), 2.65 (1H, dd, J=9.77, 7.09 Hz), 2.77 (1H, dd, J=8.79, 7.09 Hz), 3.12–3.18 (1H, m), 3.20 (3H, s), 3.37–3.48 (1H, m), 3.55–3.64 (1H, m), 3.65 (3H, s), 5.50 (1H, q, J=6.84 Hz), 7.28–7.37 (5H, m).

Reference Example 3-2

4-(R)-Cyclobutylcarbonyl-1-[1-(R)-phenylethyl]-2-pyrrolidone

Under a nitrogen atmosphere, cyclobutylmagnesium chloride (1 mol/l tetrahydrofuran solution, 28 ml) prepared from chlorocyclobutane was added dropwise to a tetrahydrofuran solution (50 ml) of 1-[1-(R)-phenylethyl]-5-oxopyrrolidine-3-(R)—(N-methyl-N-methoxy)carboxamide (1.93 g, 7.00 mmol), followed by stirring at room temperature for 30 minutes. To the reaction solution was added 1 mol/l hydrochloric acid (50 ml) under ice cooling and then, the mixture was extracted with ethyl acetate (80 ml×2). The organic layer was washed with saturated saline (100 ml) and then dried over anhydrous sodium sulfate. After removal of the solvent under reduced pressure, the resulting residue was subjected to silica gel column chromatography to obtain the title compound (1.47 g, 78%) as a pale yellow oil from the fraction eluted with n-hexane/ethyl acetate=1/2.

$^1$H-NMR (400 MHz, CDCl$_3$) δ: 1.53 (3H, d, J=7.33 Hz), 1.78–1.89 (1H, m), 1.92–2.06 (1H, m), 2.06–2.31 (4H, m), 2.58–2.65 (2H, m), 3.05 (1H, dd, J=9.28, 8.79 Hz), 3.13–3.21 (1H, m), 3.31 (1H, quint, J=8.30), 3.53 (1H, dd, J=9.28, 6.83 Hz), 5.48 (1H, q, J=7.33 Hz), 7.27–7.37 (5H, m).

Reference Example 3-3

4-(R)-(1-Cyclobutyl-1-hydroxy)methyl-1-[1-(R)-phenylethyl]-2-pyrrolidone

To an ethanol (40 ml) solution of 4-(R)-cyclobutylcarbonyl-1-[1-(R)-phenylethyl]-2-pyrrolidone (2.12 g, 7.80 mmol) was added sodium borohydride (295 mg) under ice cooling, followed by stirring at the same temperature for 1 hour. To the reaction solution was added 10% citric acid (50 ml) under ice cooling, and then the ethanol was removed under reduced pressure. The residue was extracted with chloroform (80 ml×2) and, after washing with saturated saline (100 ml), the organic layer was dried over anhydrous sodium sulfate. After removal of the solvent under reduced pressure, the residue was subjected to silica gel column chromatography to obtain the title compound (2.10 g, 98%) as a pale yellow oil (a mixture of isomers) from the fractions with eluents of n-hexane/ethyl acetate (1/3) to ethyl acetate.

$^1$H-NMR (400 MHz, CDCl$_3$) δ: 1.50 (3H, d, J=6.83 Hz), 1.68–2.01 (6H, m), 2.14–2.45 (3H, m), 2.45–2.56 (1H, m), 2.91–3.05 (1H, m), 3.19–3.31 (1H, m), 3.41–3.49 (1H, m), 5.42–5.49 (1H, m), 7.24–7.36 (5H, m).

Reference Example 3-4

4-(R)-(1-Azido-1-cyclobutyl)methyl-1-[1-(R)-phenylethyl]-2-pyrrolidone

Under ice cooling, triethylamine (1.36 ml, 9.80 mmol) and then methanesulfonyl chloride (640 μl, 8.30 mmol) were added to a dichloromethane (35 ml) solution of 4-(R)-(1-cyclobutyl-1-hydroxy)methyl-1-[1-(R)-phenylethyl]-2-pyrrolidone (2.05 g, 7.50 mmol), followed by stirring at the same temperature for 1 hour. To the reaction solution was added 10% citric acid (35 ml) under ice cooling, the mixture was extracted with chloroform (50 ml×2). After washing with saturated saline (150 ml), the organic layer was dried over anhydrous sodium sulfate. The solvent was removed under reduced pressure, and the residue was dissolved in N,N-dimethylformamide (30 ml) and sodium azide (1.46 g, 22.5 mmol) was added thereto, followed by stirring at 60° C. for 3 hours. After cooling on standing, water (150 ml) was added to the reaction solution and the mixture was extracted with ethyl acetate (150 ml×3). The organic layer was washed with saturated saline (150 ml) and then, dried over anhydrous sodium sulfate. After removal of the solvent under reduced pressure, the residue was subjected to silica gel column chromatography to obtain the title compound having low polarity (isomer B1) (898 mg, 40%) as a colorless oil from the fraction eluted with n-hexane/ethyl acetate=3/2 and the title compound having high polarity (isomer B2) (847 mg, 38%) as colorless crystals from the fraction eluted with n-hexane/ethyl acetate=2/3.

Isomer B1

$^1$H-NMR (400 MHz, CDCl$_3$) δ: 1.52 (3H, d, J=6.83 Hz), 1.72–2.01 (5H, m), 2.07–2.17 (1H, m), 2.26–2.41 (3H, m), 2.45–2.56 (1H, m), 2.98 (1H, dd, J=9.77, 7.81 Hz), 3.14 (1H, dd, J=9.77, 7.32 Hz), 3.32 (1H, dd, J=8.76, 3.91 Hz), 5.47 (1H, q, J=6.83 Hz), 7.25–7.35 (5H, m).

Isomer B2

$^1$H-NMR (400 MHz, CDCl$_3$) δ: 1.52 (3H, d, J=6.83 Hz), 1.75–2.03 (5H, m), 2.03–2.17 (1H, m), 2.19–2.38 (2H, m), 2.40–2.56 (2H, m), 2.99 (1H, dd, J=9.77, 8.30 Hz), 3.14 (1H, dd, J=9.77, 7.32 Hz), 3.30 (1H, dd, J=8.30, 6.34 Hz), 5.47 (1H, q, J=6.83 Hz), 7.25–7.35 (5H, m).

Reference Example 3-5

4-(R)-[1-(tert-Butoxycarbonyl)amino-1-cyclobutyl]methyl-1-[1-(R)-phenylethyl]-2-pyrrolidone (Isomer B1)

To an ethanol (50 ml) solution of 4-(R)-(1-azido-1-cyclobutyl)methyl-1-[1-(R)-phenylethyl]-2-pyrrolidone (isomer B1) (835 mg, 2.80 mmol) was added a 10% palladium-carbon catalyst (water content 53.8%, 850 mg) and catalytic hydrogenation was carried out at room temperature at normal pressure for 5 hours. The reaction solution was filtered and the solvent was removed under reduced pressure. The resulting residue was dissolved in dichloromethane (20 ml) and di-tert-butyl dicarbonate (917 mg) and triethylamine (780 μl) were added thereto, followed by stirring at room temperature for 15 hours. Chloroform (50 ml) was added to the reaction solution, the solution was washed with 10% citric acid (80 ml) and water (80 ml), and then the organic layer was dried over anhydrous sodium sulfate. After removal of the solvent under reduced pressure, the residue was subjected to silica gel column chromatography to obtain the title compound (809 mg, 78%) as white amorphous from the fractions eluted with n-hexane/ethyl acetate of from 3/2 to 1/1.

$^1$H-NMR (400 MHz, CDCl$_3$) δ: 1.44 (9H, s), 1.48 (3H, d, J=7.32 Hz), 1.66–1.98 (6H, m), 2.17–2.43 (4H, m), 2.94–3.03 (1H, m), 3.09–3.18 (1H, m), 3.59–3.68 (1H, m), 4.46–4.58 (1H, m), 5.46 (1H, q, J=7.32 Hz), 7.27–7.35 (5H, m).

Reference Example 3-6

3-(R)-[1-(tert-Butoxycarbonyl)amino-1-cyclobutyl)methyl-1-[1-(R)-phenylethyl]pyrrolidine (Isomer B1)

Under a nitrogen atmosphere, 1 mol/l borane-tetrahydrofuran complex solution (5.6 ml) was added dropwise to a tetrahydrofuran solution (15 ml) of 4-(R)-[1-(tert-butoxycarbonyl)amino-1-cyclobutyl]methyl-1-[1-(R)-phenylethyl]-2-pyrrolidone (isomer B1) (700 mg, 1.88 mmol) under ice cooling, followed by stirring at room temperature for 13 hours. After removal of the solvent under reduced pressure, 80% water-containing ethanol (15 ml) and triethylamine (3 ml) were added to the residue and the mixture was heated under reflux for 4 hours. After cooling on standing, the solvent was removed under reduced pressure and chloroform (30 ml) was added to the resulting residue. The solution was washed with water (10 ml) and saturated saline (10 ml) and then, dried over anhydrous sodium sulfate. After removal of the solvent under reduced pressure, the resulting residue was subjected to silica gel column chromatography to obtain the title compound (565 mg, 84%) as colorless crystals from the fraction eluted with chloroform/methanol=20/1.

$^1$H-NMR (400 MHz, CDCl$_3$) δ: 1.36 (3H, d, J=6.84 Hz), 1.45 (9H, s), 1.66–1.95 (7H, m), 2.05–2.22 (2H, m), 2.22–2.34 (1H, m), 2.34–2.45 (2H, m), 3.15 (1H, q, J=6.84 Hz), 3.43–3.53 (1H, m), 4.54–4.62 (1H, m), 7.21–7.31 (5H, m).

Reference Example 3-7

3-(R)-[1-(tert-Butoxycarbonyl)amino-1-cyclobutyl]methylpyrrolidine (Isomer B1)

To an ethanol (30 ml) solution of 3-(R)-[1-(tert-butoxycarbonyl)amino-1-cyclobutyl]methyl-1-[1-(R)-phenylethyl]pyrrolidine (isomer B1) (516 mg, 1.44 mmol) was added a 10% palladium-carbon catalyst (water content 53.8%, 500 mg) and catalytic hydrogenation was carried out under heating at an outer temperature of 50° C. at normal pressure for 5 hours. The reaction solution was filtered and the solvent was removed under reduced pressure to obtain the title compound (366 mg, quantitative) as colorless crystals.

Reference Example 4

6-Fluoro-1-[2-(S)-fluoro-1-(R)-cyclopropyl]-1,4-dihydro-8-methoxy-7-(4-methylpiperazin-1-yl)-4-oxoquinoline-3-carboxylic acid (Compound 15)

To dry dimethyl sulfoxide (18 ml) was added 1-methylpiperazine (1.55 ml, 14.0 mmol) and triethylamine (1.95 ml, 14 mmol), and then, 6,7-difluoro-1-[2-(S)-fluoro-1-(R)-cyclopropyl]-1,4-dihydro-8-methoxy-4-oxoquinoline-3-carboxylic acid-BF$_2$ chelate (3.61 g, 10.0 mmol) was added thereto, followed by stirring at room temperature for 22 hours. After concentration of the reaction solution under reduced pressure, the residue was suspended into a solution (110 ml) of ethanol/water=9/1 and then triethylamine (2 ml) was added thereto, followed by heating under reflux for 2 hours. After cooling on standing, the reaction solution was concentrated under reduced pressure. Conc. hydrochloric acid (20 ml) was added dropwise to the residue under ice cooling and then, the mixture was stirred at room temperature for 30 minutes. To the reaction solution was added 1 mol/l hydrochloric acid (5 ml), and the resulting yellow acidic aqueous solution was washed with chloroform (50 ml×4). Thereafter, the solution was rendered pH 12.0 by sodium hydroxide aqueous solution. The basic solution was adjusted to pH 7.4 by 1 mol/l hydrochloric acid and then, extracted with chloroform (150 ml×5). After drying over anhydrous sodium sulfate, the solvent was removed under reduced pressure. The resulting residue was recrystallized from isopropyl alcohol to obtain the title compound (2.98 g, 7.58 mmol, 76%) as yellow crystals.

$^1$H-NMR (400 MHz, 0.1 mol/l-NaOD) δ: 1.37–1.53 (2H, m), 2.17 (3H, s), 2.43–2.48 (4H, m), 3.17–3.22 (4H, m), 3.63–3.68 (3H, m), 3.90–3.94 (1H, m), 4.82 (1H, dm, J=62.0 Hz), 7.59 (1H, d, J=12.7 Hz), 8.40 (1H, s). IR (KBr disk): 2931, 2841, 2817, 2796, 1898, 1768, 1722, 1622, 1603, 1512, 1462, 1435, 1394, 1315, 1290, 1242, 1227, 1207 cm$^{-1}$ Melting point; 192–194° C. Elementary analysis: FW393.39 as $C_{19}H_{21}F_2N_3O_4$ Theoretical: C, 58.01%; H, 5.38%; N, 10.68% Found: C, 58.02%; H, 5.42%; N, 10.41%.

Reference Example 5

7-(3,5-cis-Dimethylpiperazin-1-yl)-6-fluoro-1-[2-(S)-fluoro-1-(R)-cyclopropyl]-1,4-dihydro-8-methoxy-4-oxoquinoline-3-carboxylic acid
(Compound 16)

To dry dimethyl sulfoxide (10 ml) was added cis-2,6-dimethylpiperazine (1.14 g, 10.0 mmol) and triethylamine (1.05 ml, 7.5 mmol), and then, 6,7-difluoro-1-[2-(S)-fluoro-1-(R)-cyclopropyl]-1,4-dihydro-8-methoxy-4-oxoquinoline-3-carboxylic acid-$BF_2$ chelate (1.81 g, 5.00 mmol) was added thereto, followed by stirring at room temperature for 5 days. After concentration of the reaction solution under reduced pressure, the residue was suspended into a solution (50 ml) of ethanol/water=9/1 and then triethylamine (1 ml) was added thereto, followed by heating under reflux for 3 hours. After cooling on standing, the reaction solution was concentrated under reduced pressure. Conc. hydrochloric acid (10 ml) was added dropwise to the residue under ice cooling and then, the mixture was stirred at room temperature for 30 minutes. To the reaction solution was added 1 mol/l hydrochloric acid (5 ml), and the resulting yellow acidic aqueous solution was washed with chloroform (50 ml×4). Thereafter, the solution was rendered pH 12.0 by sodium hydroxide aqueous solution. The basic solution was adjusted to pH 7.4 by 1 mol/l hydrochloric acid and then, extracted with chloroform (150 ml×3). After drying over anhydrous sodium sulfate, the solvent was removed under reduced pressure. The resulting residue was recrystallized from ethanol to obtain the title compound (1.27 g, 3.12 mmol, 62%) as yellow crystals.

$^1$H-NMR (400MHz, 0.1 mol/l-NaOD) δ: 1.06 (3H, s), 1.07 (3H, s), 1.50–1.68 (2H, m), 2.77 (1H, t, J=11.0 Hz), 2.87 (1H, t, 10.0 Hz), 2.99–3.06 (2H, m), 3.28–3.35 (2H, m), 3.75 (3H, s), 4.02–4.07 (1H, m), 4.97 (1H, dm, J=64.1 Hz), 7.72 (1H, d, J=12.7 Hz), 8.50 (1H, s). Melting point; 129–131° C. Elementary analysis: FW425.43 as $C_{20}H_{23}F_2N_3O_4 \cdot 1H_2O$ Theoretical: C, 56.46%; H, 5.92%; N, 9.88% Found: C, 56.72%; H, 5.92%; N, 9.85%.

Reference Example 6

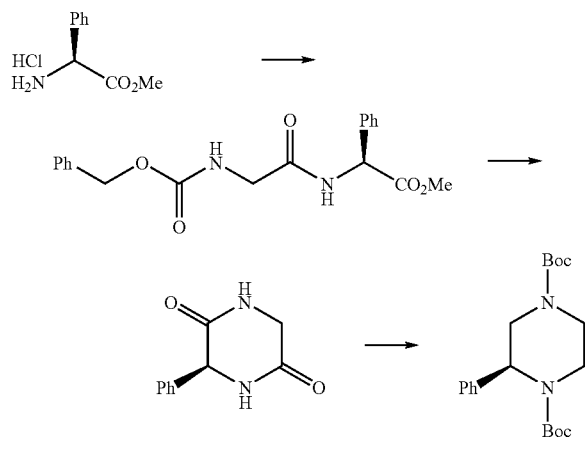

Reference Example 6-1

Carbobenzyloxyglycyl-(2S)-phenylglycine methyl ester

Sodium hydrogen carbonate (2.82 g) was added to a mixed solution of water (12 ml) and tetrahydrofuran (12 ml) of (S)-(+)-2-phenylglycine methyl ester hydrochloride (1.84 g, 9.1 mmol), and then, a THF (10 ml) solution of carbobenzyloxyglycinesuccinimide (3.06 g, 10 mmol) was added dropwise thereto under ice cooling. After stirring at the same temperature for 30 minutes, the mixture was stirred at room temperature for another 20 hours. After removal of the solvent under reduced pressure, ethyl acetate was added to the residue and, after washing with water, the organic layer was dried over anhydrous sodium sulfate. Under reduced pressure, the solvent was removed to obtain the title compound (3.56 g, quantitative).

$^1$H-NMR (400 MHz, 0.1 mol/l-NaOD) δ: 3.72 (3H, s), 3.84–4.01 (2H, m), 5.14 (2H, s), 5.40 (1H, brs), 5.56 (1H, d, J=7.20 Hz), 7.02 (1H, brs), 7.33 (10H, s).

Reference Example 6-2

2,5-Dioxo-(3S)-phenylpiperazine

To an ethanol (300 ml) solution of carbobenzyloxyglycyl-(2S)-phenylglycine methyl ester (2) (18 g, 50.51 mmol) was added 10% palladium/carbon (water content 50%, 18 g), and catalytic reduction was carried out at 50° C. at 1 atm for 18 hours. The palladium/carbon catalyst was separated by filtration, and the solvent of the filtrate was removed by evaporation to obtain a crude product of the title compound. This product was used in the next reaction without purification.

Reference Example 6-3

1,4-di-tert-Butoxycarbonyl-(2S)-phenylpiperazine

To a THF (200 ml) suspension of the above-described 2,5-dioxo-(3S)-phenylpiperazine (3) was added dropwise a tetrahydrofuran solution (250 ml) of 1 mol/l borane-tetrahydrofuran complex under ice cooling, followed by stirring at room temperature for 15 hours. After addition of methanol (about 10 ml) under ice cooling, the mixture was stirred at room temperature for 30 minutes. After removal of the solvent under reduced pressure, the residue was suspended into a mixed solvent (300 ml) of ethanol/water (4/1), and then triethylamine (50 ml) was added thereto, followed by heating under reflux for 3 hours. After cooling on standing, the reaction solution was concentrated under reduced pressure. The residue was dissolved in a mixed solvent (500 ml) of tetrahydrofuran/dichloromethane (1/1). After addition of triethylamine (about 50 ml), di-tert-butyl dicarbonate (30 g) and catalytic amount of 4-dimethylaminopyridine were added thereto, followed by stirring at room temperature for 5 hours. After removal of the solvent under reduced pressure, the residue was dissolved in chloroform, and then, the solution was washed with 10% citric acid aqueous solution (50 ml×3). The organic layer was dried over anhydrous sodium sulfate and then, the solvent was removed under reduced pressure. The resulting residue was subjected to silica gel column chromatography and elution with hexane/ethyl acetate (7/1) afforded the title compound (5.04 g, 28% from Compound (2)) as colorless crystals.

$^1$H-NMR (400 MHz, 0.1 mol/l-NaOD) δ: 1.43 (9H, s), 1.46 (9H, s), 2.90–3.15 (2H, m), 3.30–3.39 (1H, m), 3.92–4.03 (2H, m), 4.38–4.50 (1H, m), 5.35 (1H, brs), 7.21–7.40 (5H, m).

Example 1

6-Fluoro-1-[(1R,2S)-2-fluorocyclopropyl]-7-(3-fluoromethylpiperazin-1-yl)-1,4-dihydro-8-methoxy-4-oxoquinoline-3-carboxylic acid (Compound 19)

To dimethyl sulfoxide (2 ml) was added 3-fluoromethylpiperazine (184 mg, 1.56 mmol), and then, triethylamine (619 μl, 4.44 mmol) and 6,7-difluoro-1-[(1R,2S)-2-fluorocyclopropyl]-1,4-dihydro-8-methoxy-4-oxoquinoline-3-carboxylic acid-$BF_2$ chelate (668 mg, 1.85 mmol) were added thereto. After stirring at room temperature for 15 hours, the solvent and the triethylamine were removed under reduced pressure. The residue was suspended into a mixed solvent (100 ml) of ethanol/water (9/1) and then triethylamine (1 ml) was added thereto, followed by heating under reflux for 1 hour. After cooling on standing, the reaction solution was concentrated under reduced pressure. Conc. hydrochloric acid (about 10 ml) was added dropwise to the residue under ice cooling to dissolve it and then, the solution was washed with chloroform (100 ml×3). Thereafter, the solution was rendered pH 11.0 by sodium hydroxide aqueous solution, and then, the solution was adjusted to pH 7.4 by conc. hydrochloric acid and 1 mol/l hydrochloric acid. The aqueous layer was extracted with chloroform (150 ml×3). After drying over anhydrous sodium sulfate, the solvent was removed under reduced pressure. The resulting residue was separated and purified by preparative TLC and then, recrystallized from methanol-diethyl ether to obtain the title compound (293 mg, 46%) as pale yellow crystals.

Melting point; 153–156° C. $^1$H-NMR (400 MHz, 0.1 mol/l-NaOD) δ: 1.50–1.67 (2H, m), 2.98–3.43 (7H, m), 3.76–3.82 (3H, m), 4.04–4.06 (1H, m), 4.43–4.58 (2H, m), 4.96 (1H, dm, J=67.28 Hz), 7.71–7.76 (1H, m), 8.51 (1H, s). Elementary analysis: as $C_{19}H_{20}F_3N_3O_4 \cdot 0.25H_2O$ Theoretical: C, 54.87%; H, 4.97%; N, 10.10% Found: C, 54.84%; H, 4.92%; N, 10.02%.

Example 2

6-Fluoro-1-[(1R,2S)-2-fluorocyclopropyl]-7-(3,3'-difluoromethylpiperazin-1-yl)-1,4-dihydro-8-methoxy-4-oxoquinoline-3-carboxylic acid (Compound 20)

To dimethyl sulfoxide (1.5 ml) was added 3,3'-difluoromethylpiperazine (146 mg, 1.07 mmol), and then, triethylamine (460 μl, 3.30 mmol) and 6,7-difluoro-1-[(1R,2S)-2-fluorocyclopropyl]-1,4-dihydro-8-methoxy-4-oxoquinoline-3-carboxylic acid-$BF_2$ chelate (361 mg, 1.00 mmol) were added thereto. After stirring at room temperature for 14 hours, the solvent and the triethylamine were removed under reduced pressure. The residue was suspended into a mixed solvent (20 ml) of ethanol/water (9/1) and then triethylamine (1 ml) was added thereto, followed by heating under reflux for 2 hours. After cooling on standing, the reaction solution was concentrated under reduced pressure. Conc. hydrochloric acid (about 5 ml) was added dropwise to the residue under ice cooling to dissolve it and then, the solution was washed with chloroform (50 ml×3). Thereafter, the solution was rendered pH 11.0 by sodium hydroxide aqueous solution, and then, the solution was adjusted to pH 7.4 by conc. hydrochloric acid and 1 mol/l hydrochloric acid. The aqueous layer was extracted with chloroform (100 ml×3). After drying over anhydrous sodium sulfate, the solvent was removed under reduced pressure. The resulting residue was separated and purified by preparative TLC and then, recrystallized from isopropyl alcohol-diethyl ether to obtain the title compound (65 mg, 15%) as pale yellow crystals.

Melting point; 164–166° C. $^1$H-NMR (400 MHz, 0.1 mol/l-NaOD) δ: 1.53–1.65 (2H, m), 2.99–3.56 (7H, m), 3.82 (3H, d, J=3.41 Hz), 4.06–4.08 (1H, m), 4.96 (1H, dm, J=64.59 Hz), 5.95 (1H, t, J=55.21 Hz), 7.75 (1H, d, J=12.68 Hz), 8.51 (1H, s). Elementary analysis: as $C_{19}H_{19}F_4N_3O_4 \cdot 0.25H_2O$ Theoretical: C, 52.60%; H, 4.53%; N, 9.68% Found: C, 52.75%; H, 4.54%; N, 9.60%.

Example 3

6-Fluoro-1-[(1R,2S)-2-fluorocyclopropyl]-1,4-dihydro-8-methoxy-7-(3-methoxymethylpiperazin-1-yl)-4-oxoquinoline-3-carboxylic acid (Compound 21)

To dimethyl sulfoxide (3 ml) was added 3-methoxymethylpiperazine (399 mg, 3.06 mmol), and then, triethylamine (853 μl, 6.12 mmol) and 6,7-difluoro-1-[(1R,2S)-2-fluorocyclopropyl]-1,4-dihydro-8-methoxy-4-oxoquinoline-3-carboxylic acid-$BF_2$ chelate (921 mg, 2.55 mmol) were added thereto. After stirring at room temperature for 11.5 hours, the solvent and the triethylamine were removed under reduced pressure. The residue was suspended into a mixed solvent (100 ml) of ethanol/water (9/1) and then triethylamine (2 ml) was added thereto, followed by heating under reflux for 3 hours. After cooling on standing, the reaction solution was concentrated under reduced pressure. Conc. hydrochloric acid (about 10 ml) was added dropwise to the residue under ice cooling to dissolve it and then, the solution was washed with chloroform (100 ml×3). Thereafter, the solution was rendered pH 11.0 by sodium hydroxide aqueous solution, and then, the solution was adjusted to pH 7.4 by conc. hydrochloric acid and 1 mol/l hydrochloric acid. The aqueous layer was extracted with chloroform (150 ml×3). After drying over anhydrous sodium sulfate, the solvent was removed under reduced pressure. The resulting residue was separated and purified by preparative TLC and then, recrystallized from methanol-diethyl ether to obtain the title compound (680 mg, 63%) as pale yellow crystals.

Melting point; 92–95° C. $^1$H-NMR (400 MHz, 0.1 mol/l-NaOD) δ: 1.50–1.63 (2H, m), 2.97–3.47 (9H, m), 3.39–3.41 (3H, m), 3.77–3.81 (3H, m), 4.03–4.05 (1H, m), 4.95 (1H, dm, J=64.35 Hz), 7.72 (1H, d, J=12.19 Hz), 8.50 (1H, s). Elementary analysis: as $C_{20}H_{23}F_2N_3O_5 \cdot 0.5H_2O$ Theoretical: C, 55.55%; H, 5.59%; N, 9.72% Found: C, 55.41%; H, 5.61%; N, 9.63%.

Example 4

7-{4,7-Diazaspiro[2.5]octan-7-yl}-6-fluoro-1-[(1R,2S)-2-fluorocyclopropyl]-1,4-dihydro-8-methoxy-4-oxoquinoline-3-carboxylic acid (Compound 22)

To dimethyl sulfoxide (0.5 ml) was added 4,7-diazaspiro[2.5]octane (61.2 mg, 0.546 mmol), and then, 6,7-difluoro-1-[(1R,2S)-2-fluorocyclopropyl]-1,4-dihydro-8-methoxy-4-oxoquinoline-3-carboxylic acid-$BF_2$ chelate (179 mg, 0.496 mmol) and triethylamine (251 μl, 1.64 mmol) were added thereto. After stirring at room temperature for 15 hours, the solvent and the triethylamine were removed under reduced pressure. The residue was suspended into a mixed solvent (20 ml) of ethanol/water (9/1) and then triethylamine (1 ml) was added thereto, followed by heating under reflux for 3 hours. After cooling on standing, the reaction solution was concentrated under reduced pressure. Conc. hydrochloric acid (about 2 ml) was added dropwise to the residue under ice cooling to dissolve it and then, 1 mol/l hydrochloric acid (about 2 ml) was added, followed by washing with chloroform (50 ml×3). Thereafter, the solution was rendered pH 11.0 by sodium hydroxide aqueous solution, and then, the solution was adjusted to pH 7.4 by conc. hydrochloric acid and 1 mol/l hydrochloric acid. The aqueous layer was extracted with chloroform (50 ml×3). After drying over anhydrous sodium sulfate, the solvent was removed under reduced pressure. The resulting residue was separated and purified by preparative TLC and then, recrystallized from isopropyl alcohol-diethyl ether to obtain the title compound (40.0 mg, 20%) as pale yellow crystals.

Melting point; 164–167° C. (decomp.) $^1$H-NMR (400 MHz, 0.1 mol/l-NaOD) δ: 0.64–0.67 (4H, m), 1.50–1.68 (2H, m), 3.02–3.19 (3H, m), 3.21–3.40 (3H, m), 3.83 (3H, s), 4.01–4.05 (1H, m), 4.95 (1H, dm, J=60.25 Hz), 7.72 (1H, d, J=12.98 Hz), 8.49 (1H, s). Elementary analysis: as $C_{20}H_{21}F_2N_3O_4 \cdot 1H_2O$ Theoretical: C, 56.73%; H, 5.48%; N, 9.92% Found: C, 57.11%; H, 5.29%; N, 9.63%.

Example 5

7-{5,8-Diazaspiro[3.5]nonan-7-yl}-6-fluoro-1-[(1R,2S)-2-fluorocyclopropyl]-1,4-dihydro-8-methoxy-4-oxoquinoline-3-carboxylic acid (Compound 23)

To dimethyl sulfoxide (1.5 ml) was added 5,8-diazaspiro[3.5]nonane (171 mg, 1.36 mmol), and then, 6,7-difluoro-1-[(1R,2S)-2-fluorocyclopropyl]-1,4-dihydro-8-methoxy-4-oxoquinoline-3-carboxylic acid-BF$_2$ chelate (491 mg, 1.36 mmol) and triethylamine (626 μl, 4.49 mmol) were added thereto. After stirring at 40° C. for 22 hours, the solvent and the triethylamine were removed under reduced pressure. The residue was suspended into a mixed solvent (20 ml) of ethanol/water (9/1) and then triethylamine (0.5 ml) was added thereto, followed by heating under reflux for 2 hours. After cooling on standing, the reaction solution was concentrated under reduced pressure. Conc. hydrochloric acid (about 2 ml) was added dropwise to the residue under ice cooling to dissolve it and then, 1 mol/l hydrochloric acid (about 2 ml) was added, followed by washing with chloroform (50 ml×3). Thereafter, the solution was rendered pH 12.0 by sodium hydroxide aqueous solution, and then, the solution was adjusted to pH 7.4 by conc. hydrochloric acid and 1 mol/l hydrochloric acid. The aqueous layer was extracted with chloroform (100 ml×4). After drying over anhydrous sodium sulfate, the solvent was removed under reduced pressure. The resulting residue was separated and purified by preparative TLC and then, recrystallized from isopropyl alcohol-diethyl ether to obtain the title compound (67.2 mg, 12%) as pale yellow crystals.

Melting point; 138–140° C. (decomp.) $^1$H-NMR (400 MHz, 0.1 mol/l-NaOD) δ: 1.51–2.07 (8H, m), 2.90–2.92 (2H, m), 3.26–3.31 (4H, m), 3.78 (3H, s), 4.06–4.07 (1H, m), 4.97 (1H, dm, J=63.11 Hz), 7.74 (1H, d, J=13.31 Hz), 8.51 (1H, s). Elementary analysis: as $C_{21}H_{23}F_2N_3O_4 \cdot 1.5H_2O$ Theoretical: C, 56.50%; H, 5.87%; N, 9.41% Found: C, 56.52%; H, 5.55%; N, 9.24%.

Example 6

7-(3-Cyclopropylpiperazin-1-yl)-6-fluoro-1-[(1R,2S)-2-fluorocyclopropyl]-1,4-dihydro-8-methoxy-4-oxoquinoline-3-carboxylic acid (Compound 24)

To dimethyl sulfoxide (0.5 ml) was added 3-cyclopropylpiperazine (60.3 mg, 0.478 mmol), and then, triethylamine (220 μl, 1.58 mmol) and 6,7-difluoro-1-[(1R,2S)-2-fluorocyclopropyl]-1,4-dihydro-8-methoxy-4-oxoquinoline-3-carboxylic acid-BF$_2$ chelate (173 mg, 0.478 mmol) were added thereto. After stirring at 40° C. for 12 hours, the solvent and the triethylamine were removed under reduced pressure. The residue was suspended into a mixed solvent (20 ml) of ethanol/water (9/1) and then triethylamine (0.5 ml) was added thereto, followed by heating under reflux for 2 hours. After cooling on standing, the reaction solution was concentrated under reduced pressure. Conc. hydrochloric acid (about 5 ml) was added dropwise to the residue under ice cooling to dissolve it and then, the solution was washed with chloroform (50 ml×3). Thereafter, the solution was rendered pH 11.0 by sodium hydroxide aqueous solution, and then, the solution was adjusted to pH 7.4 by conc. hydrochloric acid and 1 mol/l hydrochloric acid. The aqueous layer was extracted with chloroform (100 ml×4). After drying over anhydrous sodium sulfate, the solvent was removed under reduced pressure. The resulting residue was separated and purified by preparative TLC and then, recrystallized from isopropyl alcohol-diethyl ether to obtain the title compound (36.4 mg, 18%) as pale yellow crystals.

Melting point; 136–139° C. $^1$H-NMR (400 MHz, 0.1 mol/l-NaOD) δ: 0.26–0.28 (2H, m), 0.50–0.52 (2H, m), 0.78–0.80 (1H, m), 1.51–1.60 (2H, m), 2.07–2.09 (1H, m), 2.93–3.46 (6H, m), 3.78 (3H, d, J=7.57 Hz), 4.06–4.07 (1H, m), 4.95 (1H, dm J=61.89 Hz), 7.73 (1H, d, J=10.13 Hz), 8.50 (1H, s). Elementary analysis: as $C_{21}H_{23}F_2N_3O_4 \cdot 1.25H_2O$ Theoretical: C, 57.07%; H, 5.82%; N, 9.51% Found: C, 57.16%; H, 5.57%; N, 9.43%.

Example 7

1-Cyclopropyl-6-fluoro-1,4-dihydro-8-methoxy-7-[(3S)-phenylpiperazin-1-yl]-4-oxoquinoline-3-carboxylic acid (Compound 25)

Trifluoroacetic acid (3 ml) was added to a dichloromethane (2 ml) solution of 1,4-di-tert-butoxycarbonyl-(2S)-phenylpiperazine (507 mg, 1.40 mmol), and then, the reaction solution was stirred at room temperature for 15 minutes. The solvent of the reaction solution and the trifluoroacetic acid were removed under reduced pressure and the residue was dissolved in dimethyl sulfoxide (4 ml). Thereafter, 1-cyclopropyl-6,7-difluoro-1,4-dihydro-8-methoxy-4-oxoquinoline-3-carboxylic acid-BF$_2$ chelate (343 mg, 1.00 mmol) and triethylamine (1 ml) were added thereto. After stirring at room temperature for 70 hours, the solvent and the triethylamine were removed under reduced pressure. The residue was suspended into a mixed solvent (100 ml) of ethanol/water (4/1) and then triethylamine (10 ml) was added thereto, followed by heating under reflux for 6 hours. After cooling on standing, the reaction solution was concentrated under reduced pressure. Conc. hydrochloric acid (about 10 ml) was added dropwise to the residue under ice cooling to dissolve it and then, the solution was stirred at room temperature for 5 minutes. Thereafter, the solution was rendered pH 12.0 by sodium hydroxide aqueous solution, and then, the solution was adjusted to pH 7.2 by conc. hydrochloric acid and 1 mol/l hydrochloric acid. The aqueous layer was extracted with chloroform (100 ml×3). After drying over anhydrous sodium sulfate, the solvent was removed under reduced pressure. The resulting residue was recrystallized from 28% aqueous ammonia-ethanol to obtain the title compound (280 mg, 64%) as pale yellow crystals.

Melting point; 114–121° C. $^1$H-NMR (400 MHz, 0.1 mol/l-NaOD) δ: 0.60–0.70 (1H, m), 0.71–0.77 (1H, m), 0.95–1.07 (2H, m), 2.95–3.35 (6H, m), 3.66 (3H, s), 3.71–3.95 (2H, m), 7.08–7.33 (5H, m), 7.66 (1H, d, J=12.70 Hz), 8.46 (1H, s). Elementary analysis: as $C_{24}H_{24}FN_3O_4 \cdot 0.25H_2O$ Theoretical: C, 65.22%; H, 5.59%; N, 9.51% Found: C, 65.09%; H, 5.51%; N, 9.46%.

Example 8

6-Fluoro-1-[(1R,2S)-2-fluorocyclopropyl]-1,4-dihydro-8-methoxy-7-[(3S)-phenylpiperazin-1-yl]-4-oxoquinoline-3-carboxylic acid hydrochloride
(Compound 26)

Trifluoroacetic acid (3 ml) was added to a dichloromethane (2 ml) solution of 1,4-di-tert-butoxycarbonyl-(2S)-phenylpiperazine (695 mg, 1.92 mmol), and then, the reaction solution was stirred at room temperature for 15 minutes. The solvent of the reaction solution and the trifluoroacetic acid were removed under reduced pressure and the residue was dissolved in dimethyl sulfoxide (5 ml). Thereafter, 6,7-difluoro-1-[(1R,2S)-2-fluorocyclopropyl]-1,4-dihydro-8-methoxy-4-oxoquinoline-3-carboxylic acid-$BF_2$ chelate (433 mg, 1.20 mmol) and triethylamine (1 ml) were added thereto. After stirring at room temperature for 15 hours, the solvent and the triethylamine were removed under reduced pressure. The residue was suspended into a mixed solvent (100 ml) of ethanol/water (4/1) and then triethylamine (10 ml) was added thereto, followed by heating under reflux for 2 hours. After cooling on standing, the reaction solution was concentrated under reduced pressure. Conc. hydrochloric acid (about 10 ml) was added dropwise to the residue under ice cooling to dissolve it and then, the solution was stirred at room temperature for 5 minutes. Thereafter, the solution was rendered pH 12.0 by sodium hydroxide aqueous solution, and then, the solution was adjusted to pH 7.3 by conc. hydrochloric acid and 1 mol/l hydrochloric acid. The aqueous layer was extracted with chloroform (100 ml×3). After drying over anhydrous sodium sulfate, the solvent was removed under reduced pressure. The resulting residue was separated and purified by preparative TLC and then, converted into the hydrochloride by using equivalent amount of 1 mol/l hydrochloric acid. The salt was recrystallized from ethanol-diethyl ether to obtain the title compound (345 mg, 60%) as pale yellow crystals.

Melting point; 194–203° C. $^1$H-NMR (400 MHz, 0.1 mol/l-NaOD) δ: 1.26–1.35 (1H, m), 1.40–1.51 (1H, m), 2.88–3.06 (3H, m), 3.09–3.32 (3H, m), 3.64 (3H, s), 3.75–3.90 (2H, m), 4.60–4.70 (0.5H, m), 7.12–7.30 (5H, m), 7.63 (1H, d, J=12.70 Hz), 8.44 (1H, s). Elementary analysis: as $C_{24}H_{23}F_2N_3O_4 \cdot HCl \cdot 1.75H_2O$ Theoretical: C, 55.07%; H, 5.30%; N, 8.03% Found: C, 55.04%; H, 5.24%; N, 7.96%.

Example 9

9-Fluoro-2,3-dihydro-3-(S)-methyl-7-oxo-10-[3-(S)-phenyl-1-piperazinyl]-7H-pyrido[1.2.3-de][1,4]benzoxazine-6-carboxylic acid (Compound 27)

Trifluoroacetic acid (3 ml) was added to a dichloromethane (2 ml) solution of 1,4-di-tert-butoxycarbonyl-(2S)-phenylpiperazine (544 mg, 1.50 mmol), and then, the reaction solution was stirred at room temperature for 15 minutes. The solvent of the reaction solution and the trifluoroacetic acid were removed under reduced pressure and the residue was dissolved in dimethyl sulfoxide (4 ml). Thereafter, 9,10-difluoro-2,3-dihydro-(3S)-methyl-7-oxo-7H-pyrido[1.2.3-de][1,4]benzoxazine-6-carboxylic acid-$BF_2$ chelate (411 mg, 1.25 mmol) and triethylamine (1 ml) were added thereto. After stirring at room temperature for 21 hours, the solvent and the triethylamine were removed under reduced pressure. The residue was suspended into a mixed solvent (100 ml) of ethanol/water (4/1) and then triethylamine (10 ml) was added thereto, followed by heating under reflux for 3 hours. After cooling on standing, the reaction solution was concentrated under reduced pressure. Conc. hydrochloric acid (about 10 ml) was added dropwise to the residue under ice cooling to dissolve it and then, the solution was stirred at room temperature for 5 minutes, followed by washing with chloroform (100 ml×3). Thereafter, the solution was rendered pH 12.0 by sodium hydroxide aqueous solution, and then, the solution was adjusted to pH 7.4 by conc. hydrochloric acid and 1 mol/l hydrochloric acid. The aqueous layer was extracted with chloroform (150 ml×3). After drying over anhydrous sodium sulfate, the solvent was removed under reduced pressure. The resulting residue was recrystallized from ethanol to obtain the title compound (290 mg, 55%) as yellow crystals.

Melting point; 238–244° C. $^1$H-NMR (400 MHz, 0.1 mol/l-NaOD) δ: 1.48 (3H, s), 3.10–3.12 (2H, m), 3.25–3.32 (4H, m), 3.98–4.00 (1H, m), 4.32–4.35 (1H, m), 4.47–4.51 (1H, m), 4.57–4.59 (1H, m), 7.37–7.54 (6H, m), 8.34 (1H, s). Elementary analysis: as $C_{23}H_{22}FN_3O_4 \cdot 0.25H_2O$ Theoretical: C, 64.55%; H, 5.30%; N, 9.82% Found: C, 64.71%; H, 5.23%; N, 9.86%.

Example 10

7-{1,4-Diazabicyclo[3.2.1]octan-4-yl}-6-fluoro-1-[(1R,2S)-2-fluorocyclopropyl]-1,4-dihydro-8-methoxy-4-oxoquinoline-3-carboxylic acid
(Compound 28)

To dimethyl sulfoxide (4 ml) was added 1,4-diazabicyclo[3.2.1]octane dihydrochloride (828 mg, 4.47 mmol), and then, triethylamine (1.87 ml, 13.4 mmol) and 6,7-difluoro-1-[(1R,2S)-2-fluorocyclopropyl]-1,4-dihydro-8-methoxy-4-oxoquinoline-3-carboxylic acid-$BF_2$ chelate (1.35 g, 3.73 mmol) were added thereto. After stirring at room temperature for 15 hours and at 40° C. for 9 hours, the solvent and the triethylamine were removed under reduced pressure. The residue was suspended into a mixed solvent (100 ml) of ethanol/water (9/1) and then triethylamine (3 ml) was added thereto, followed by heating under reflux for 3 hours. After cooling on standing, the reaction solution was concentrated under reduced pressure. Conc. hydrochloric acid (about 20 ml) was added dropwise to the residue under ice cooling to dissolve it and then, the solution was washed with chloroform (100 ml×3). Thereafter, the solution was rendered pH 11.0 by sodium hydroxide aqueous solution, and then, the solution was adjusted to pH 7.4 by conc. hydrochloric acid and 1 mol/l hydrochloric acid. The aqueous layer was extracted with chloroform (100 ml×3) and chloroform/methanol (8/2) (100 ml×2). After drying over anhydrous sodium sulfate, the solvent was removed under reduced pressure. The resulting residue was recrystallized from isopropyl alcohol-diethyl ether to obtain the title compound (646 mg, 43%) as pale yellow crystals.

Melting point; 195–198° C. (decomp.) $^1$H-NMR (400 MHz, 0.1 mol/1-NaOD) δ: 1.40–1.65 (2H, m), 2.05–2.18 (2H, m), 2.57–2.74 (2H, m), 2.91–3.26 (5H, m), 3.58–3.60 (1H, m), 3.75 (3H, d, J=3.66 Hz), 4.05–4.07 (2H, m), 4.95 (1H, ddm, J=17.94, 61.89 Hz), 7.70 (1H, d, J=11.48 Hz), 8.48 (1H, d, J=19.53 Hz). Elementary analysis: as $C_{20}H_{21}F_2N_3O_4 \cdot 0.5H_2O$ Theoretical: C, 57.97%; H, 5.35%; N, 10.14% Found: C, 58.26%; H, 5.28%; N, 10.07%.

Antibacterial activity of the compounds of the invention was measured in accordance with the method described in the literature of Antimicrob. Agents and Chemother., 38, 2877 (1994), and the results are shown in Tables 3 to 8 in terms of MIC (μg/ml). In the tables, "OFLX" is an abbreviation of "OFLOXAIN".

TABLE 3

Antibacterial activity against *M. avium* and *M. intracellulare*

| | M. avium | | | | M. intracellulare | | | |
|---|---|---|---|---|---|---|---|---|
| | N-357 | N-458 | N-444 | N-472 | N-294 | N-313 | N-338 | N-345 |
| OFLX | 3.13 | 3.13 | 25 | 50 | 12.5 | 6.25 | 25 | 25 |
| RFP | 50 | 100 | 12.5 | 12.5 | 3.13 | 0.78 | 3.13 | 3.13 |
| Compd. 1 | 0.10 | 0.20 | 0.20 | 1.56 | 0.39 | 0.10 | 0.39 | 0.39 |
| Compd. 2 | 0.20 | 0.20 | 0.39 | 0.78 | 0.39 | 0.20 | 0.39 | 0.78 |
| Compd. 3 | 0.39 | 0.78 | 1.56 | 6.25 | 1.56 | 0.39 | 1.56 | 1.56 |
| Compd. 4 | 0.20 | 0.39 | 0.78 | 1.56 | 1.56 | 0.39 | 1.56 | 3.13 |
| Compd. 5 | 0.39 | 0.78 | 1.56 | 6.25 | 1.56 | 0.78 | 1.56 | 3.13 |
| Compd. 6 | 0.39 | 0.78 | 1.56 | 3.13 | 0.78 | 0.78 | 1.56 | 3.13 |
| Compd. 7 | 0.39 | 0.78 | 1.56 | 6.25 | 0.78 | 0.2 | 0.39 | 1.56 |
| Compd. 8 | 1.56 | 0.78 | 1.56 | 3.13 | 1.56 | 0.39 | 1.56 | 1.56 |
| Compd. 9 | 0.10 | 0.10 | 0.10 | 0.78 | 0.39 | 0.10 | 0.39 | 0.39 |
| Compd. 10 | 0.05 | 0.10 | 0.39 | 0.39 | 0.39 | 0.10 | 0.39 | 0.78 |
| Compd. 11 | 0.39 | 0.39 | 1.56 | 3.13 | 1.56 | 0.39 | 1.56 | 3.13 |
| Compd. 12 | 0.20 | 0.39 | 0.39 | 1.56 | 0.78 | 0.20 | 0.39 | 0.39 |
| Compd. 13 | 0.39 | 0.20 | 0.78 | 1.56 | 1.56 | 0.39 | 1.56 | 3.13 |
| Compd. 14 | 1.56 | 1.56 | 3.13 | 6.25 | 3.13 | 0.78 | 6.25 | 6.25 |
| Compd. 15 | 0.39 | 0.20 | 0.78 | 1.56 | 1.56 | 0.39 | 1.56 | 3.13 |

TABLE 4

Antibacterial activity against *M. avium* and *M. intracellulare* 2

| | M. avium | | | | M. intracellulare | | | |
|---|---|---|---|---|---|---|---|---|
| | N-357 | N-458 | N-444 | N-472 | N-294 | N-313 | N-338 | N-345 |
| OFLX | 4.0 | 4.0 | 32 | 128 | 8.0 | 1.0 | 2.0 | 2.0 |
| Compd. 16 | 0.50 | 0.50 | 1.0 | 4.0 | 1.0 | 0.12 | 0.50 | 0.50 |
| Compd. 17 | 1.0 | 1.0 | 2.0 | 8.0 | 2.0 | 0.25 | 1.0 | 1.0 |
| Compd. 18 | 0.50 | 1.0 | 2.0 | 8.0 | 2.0 | 0.25 | 0.50 | 0.50 |

TABLE 5

Antibacterial activity against *Mycobacterium tuberculosis* (RFP sensitive)

| | M. tuberculosis | | | | | |
|---|---|---|---|---|---|---|
| | H37Rv | Kurono | No. 40 | No. 41 | No. 43 | No. 68 |
| OFLX | 0.39 | 0.39 | 0.39 | 0.10 | 6.25 | 0.39 |
| RFP | 0.2 | 0.10 | 0.10 | 0.05 | 3.13 | 3.13 |
| Compd. 1 | 0.025 | 0.013 | 0.025 | <0.003 | 0.20 | 0.025 |
| Compd. 2 | 0.025 | 0.013 | 0.025 | 0.006 | 0.10 | 0.025 |
| Compd. 3 | 0.10 | 0.05 | 0.10 | 0.006 | 0.78 | 0.10 |
| Compd. 4 | 0.025 | 0.013 | 0.025 | <0.003 | 0.20 | 0.025 |
| Compd. 5 | 0.10 | 0.05 | 0.10 | 0.025 | 0.78 | 0.10 |
| Compd. 6 | 0.10 | 0.05 | 0.10 | 0.013 | 0.78 | 0.05 |
| Compd. 7 | | | | | | |
| Compd. 8 | 0.10 | 0.05 | 0.10 | 0.006 | 0.78 | 0.20 |
| Compd. 9 | 0.025 | 0.013 | 0.013 | <0.003 | 0.10 | 0.025 |
| Compd. 10 | 0.013 | 0.006 | 0.006 | <0.003 | 0.05 | 0.013 |
| Compd. 11 | 0.05 | 0.05 | 0.05 | 0.013 | 0.39 | 0.05 |
| Compd. 12 | 0.025 | 0.025 | 0.025 | 0.006 | 0.10 | 0.05 |
| Compd. 13 | 0.05 | 0.05 | 0.05 | | 1.56 | 0.10 |
| Compd. 14 | 0.20 | 0.10 | 0.20 | | 1.56 | 0.20 |
| Compd. 15 | 0.10 | 0.05 | 0.05 | 0.025 | 0.39 | 0.10 |

TABLE 6

Antibacterial activity against *Mycobacterium tuberculosis* (RFP sensitive) 2

| | M. tuberculosis | | | | | |
|---|---|---|---|---|---|---|
| | H37Rv | Kurono | No. 40 | No. 41 | No. 43 | No. 68 |
| OFLX | 1.0 | 0.50 | 1.0 | 0.25 | 8.0 | 1.0 |
| Compd. 16 | 0.12 | 0.12 | 0.12 | 0.03 | 1.0 | 0.12 |
| Compd. 17 | 0.12 | 0.12 | 0.12 | 0.06 | 2.0 | 0.25 |
| Compd. 18 | 0.12 | 0.12 | 0.12 | 0.06 | 1.0 | 0.25 |

TABLE 7

Antibacterial activity against *Mycobacterium tuberculosis* (RFP resistant)

| | RFP-resistant *M. tuberculosis* | | | | | | | |
|---|---|---|---|---|---|---|---|---|
| | No. 44 | No. 45 | No. 47 | No. 50 | No. 51 | No. 56 | No. 71 | No. 97 |
| OFLX | 1.56 | 25 | 3.13 | 0.78 | 6.25 | 12.5 | 3.13 | 12.5 |
| RFP | >100 | >100 | >100 | >100 | >100 | >100 | >100 | >100 |
| Compd. 1 | 0.05 | 0.78 | 0.20 | 0.05 | 1.56 | 6.25 | 0.20 | 0.20 |
| Compd. 2 | 0.025 | 0.39 | 0.10 | 0.05 | 0.05 | 3.13 | 0.10 | 0.20 |
| Compd. 3 | 0.10 | 3.13 | 0.78 | 0.78 | 1.56 | 6.25 | 0.78 | 3.13 |
| Compd. 4 | 0.025 | 0.78 | 0.20 | 0.20 | 0.20 | 6.25 | 0.20 | 0.78 |
| Compd. 5 | 0.20 | 12.5 | 1.56 | 0.20 | 12.5 | 50 | 1.56 | 3.13 |
| Compd. 6 | 0.20 | 3.13 | 0.39 | 0.10 | 6.25 | 50 | 0.39 | 0.78 |
| Compd. 7 | | | | | | | | |
| Compd. 8 | 0.20 | 1.56 | 0.39 | 0.39 | 0.78 | 6.25 | 0.39 | 3.13 |
| Compd. 9 | 0.05 | 0.78 | 0.20 | 0.05 | 1.56 | 3.13 | 0.2 | 0.20 |
| Compd. 10 | 0.006 | 0.20 | 0.05 | 0.025 | 0.05 | 1.56 | 0.05 | 0.10 |
| Compd. 11 | 0.10 | 1.56 | 0.78 | 0.39 | 1.56 | 6.25 | 0.39 | 3.13 |
| Compd. 12 | 0.05 | 0.78 | 0.10 | 0.10 | 0.20 | 1.56 | 0.20 | 0.39 |
| Compd. 13 | 0.10 | 0.78 | | 0.10 | | 12.5 | 0.39 | 0.78 |
| Compd. 14 | 0.78 | 6.25 | | 0.39 | | 6.25 | 1.56 | 3.13 |
| Compd. 15 | 0.20 | 1.56 | 0.39 | 0.20 | | 6.25 | 0.39 | 1.56 |

TABLE 8

Antibacterial activity against *Mycobacterium tuberculosis* (RFP resistant) 2

| | RFP-resistant *M. tuberculosis* | | | | | | | |
|---|---|---|---|---|---|---|---|---|
| | No. 44 | No. 45 | No. 47 | No. 50 | No. 51 | No. 56 | No. 71 | No. 97 |
| OFLX | 2.0 | 3.20 | 8.0 | 1.0 | 4.0 | 16 | 4.0 | 16 |
| Compd. 16 | 0.25 | 4.0 | 0.50 | 0.12 | 0.5 | 64 | 0.50 | 1.0 |
| Compd. 17 | 0.50 | 8.0 | 1.0 | 0.25 | 1.0 | 32 | 1.0 | 2.0 |
| Compd. 18 | 0.25 | 4.0 | 1.0 | 0.25 | 0.50 | 64 | 1.0 | 2.0 |
| Compd. 19 | 0.39 | 3.13 | | 0.2 | 0.78 | 50 | 1.56 | 1.56 |
| Compd. 20 | 0.39 | 6.25 | | 0.39 | 0.78 | 50 | 1.56 | 1.56 |
| Compd. 21 | 0.39 | 3.13 | | 0.39 | 0.78 | 25 | 1.56 | 1.56 |
| Compd. 22 | 0.78 | 25 | | 0.78 | 1.56 | 100 | 3.13 | 6.25 |
| Compd. 23 | 1.56 | 25 | | 1.56 | 6.25 | 100 | 12.5 | 12.5 |
| Compd. 24 | 0.78 | 12.5 | | 0.39 | 1.56 | 50 | 3.13 | 3.13 |
| Compd. 25 | 0.2 | 1.56 | | 0.1 | 0.2 | 6.25 | 0.39 | 0.78 |
| Compd. 26 | 0.1 | 1.56 | | 0.1 | 0.2 | 12.5 | 0.78 | 0.78 |
| Compd. 27 | 0.1 | 1.56 | | 0.1 | 0.2 | 6.25 | 0.39 | 0.78 |
| Compd. 28 | 0.2 | 3.13 | | 0.2 | 0.78 | 12.5 | 1.56 | 1.56 |

Mouse Acute Toxicity Test

Test Method

Male Slc:ddY mice at age of 5-weeks were used as test animals. For dissolving the compounds, 0.1 mol/l NaOH (in saline) was used. Mice were administered intravenously at a rate of 0.1 ml/30 seconds at a dosing volume of 10 ml/kg.

Peripheral Blood Micronucleus Test

Test Method

Used animals and administration method are similar to those in the mouse acute toxicity test. Samples were prepared by collecting 5 µl each of blood sample from the tail vein at 24 and 48 hours after the administration, dropping the blood on a slide at which 0.1% acridine orange solution had been applied in advance, sealing the slide with a cover glass immediately, and allowing it to stand in a refrigerator for 24 hours. The blood sample was observed for 1000 reticulocytes (RC) per individual peripheral blood sample by a fluorescence microscopy and counting micronucleus-having reticulocytes (MNRC) among them.

The results of the mouse acute toxicity test and peripheral blood micronucleous test are shown in Table 9.

TABLE 9

| Compd. No. | Concentration (mg/kg) | Mortality (dead/ test) | MNRC (%) mean ±S.E. | |
|---|---|---|---|---|
| | | | 24 hours | 48 hours |
| 15 | 50 | 0/5 | 0.20 ± 0.04 | 0.14 ± 0.04 |
| 16 | 150 | 0/5 | 0.05 ± 0.03 | 0.12 ± 0.02 |
| 27 | 100 | 0/5 | 0.20 ± 0.03 | 0.18 ± 0.04 |

Among the compounds which show high activity against a typical acid-fast bacteria and *Mycobacterium turberculosis*, all mice were survived after administration of the compounds 15, 16 and 27, and acute toxicity of these compounds was relatively weak. In addition, the compound 15, 16 or 27 showed weak micronucleus induction (untreated control: 0.12±0.08).

INDUSTRIAL APPLICABILITY

The compounds according to the invention have wide and excellent antibacterial activity, especially showing strong antibacterial activity even against rifampicin (RFP)-resistant *Mycobacterium tuberculosis*, and also possess good pharmacokinetics and safety. Accordingly, they are useful as anti acid-fast compounds.

What is claimed is:
1. A compound of the following formula:

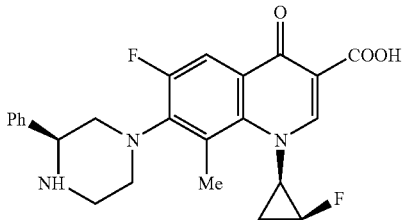

wherein Me represents a methyl group and Ph represents a phenyl group.

* * * * *